(12) United States Patent
Kompella et al.

(10) Patent No.: US 7,910,598 B2
(45) Date of Patent: Mar. 22, 2011

(54) PHENYLAMINOPYRIMIDINE DERIVATIVES AS INHIBITORS OF BCR-ABL KINASE

(75) Inventors: Amala kishan Kompella, Hyderabad (IN); Bhujanga rao Adibhatla Kali Satya, Hyderabad (IN); Sreenivas Rachakonda, Hyderabad (IN); Khadgapathi Podili, Hyderabad (IN); Nannapaneni Venkaiah Chowdary, Hyderabad (IN)

(73) Assignee: Natco Pharma Limited, Hyderabad (IN)

( * ) Notice: Subject to any disclaimer, the term of this patent is extended or adjusted under 35 U.S.C. 154(b) by 802 days.

(21) Appl. No.: 11/714,565

(22) Filed: Mar. 5, 2007

(65) Prior Publication Data

US 2007/0232633 A1   Oct. 4, 2007

Related U.S. Application Data

(63) Continuation-in-part of application No. PCT/IN2005/000243, filed on Jul. 19, 2005.

(30) Foreign Application Priority Data

Sep. 9, 2004  (IN) .............................. 908/CHE/2004

(51) Int. Cl.
*C07D 401/04* (2006.01)
*C07D 401/14* (2006.01)
*A61K 31/506* (2006.01)

(52) U.S. Cl. .......................... 514/275; 544/330; 544/331
(58) Field of Classification Search .................. 544/330, 544/331; 514/275; 564/164, 166
See application file for complete search history.

(56) References Cited

FOREIGN PATENT DOCUMENTS

| EP | 0 564 409 | 10/1993 |
|---|---|---|
| WO | WO 95/09847 | 4/1995 |
| WO | WO 99/15164 A | 4/1999 |
| WO | WO 02/22597 | 3/2002 |
| WO | WO 2004/029038 A | 4/2004 |
| WO | WO 2004/110452 A | 12/2004 |
| WO | WO 2006/027795 A1 | 3/2006 |
| WO | WO 2008/058037 * | 5/2008 |

OTHER PUBLICATIONS

Okram et al., A General Strategy for Creating "Inactive-Conformation" Abl Inhibitors, Chemistry & Biology, 13(7), pp. 779-786 (Jul. 2006).*
Okram et al., Supplemental Data: A General Strategy for Creating "Inactive-Conformation" Abl Inhibitiors, Chemistry & Biology, 13(7), pp. 1-24 (Jul. 2006).*
Ogata et al. "Synthesis and Antiviral activity of sulphonamidobenzophenone oximes and sulphonamidobenzamides." *Journal of Medicinal Chemistry.* vol. 29, No. 3. 1986. pp. 417-423.
Zimmermann et al. "Potent and selective inhibitors of the Abl-kinase: Phenylaminopyrimidine (PAP) derivatives." *Bioorganic and Medicinal Chemistry Letters.* vol. 7, No. 2. 1997. pp. 187-192.
Schindler et al. "Structural mechanism for STI-571 inhibition of Abelson tyrosine kinase." *Science.* vol. 289, No. 5486. 2000. pp. 1938-1942.
Invitation to Pay Additional Fees with Partial International Search mailed Jul. 15, 2009.
Examination Report from corresponding European Application No. 05 779 775.5-2101 dated Feb. 16, 2010.
Examination Report from corresponding European Application No. 05 779 775.5-2101 dated Apr. 25, 2008.

* cited by examiner

*Primary Examiner* — Deepak Rao
(74) *Attorney, Agent, or Firm* — Merchant & Gould P.C.

(57) ABSTRACT

The present invention relates to novel intermediates useful for the preparation of novel phenylaminopyrimidine derivatives, novel phenylaminopyrimidine derivatives. Pharmaceutical composition containing the novel phenylaminopyrimidine derivatives and processes for their preparation. The invention particularly relates to novel Phenyl pyrimidine amine derivatives of the general formula (I). The novel compounds of the formula 1 can be used in the therapy of Chronic Myeloid Leukemia (CML). Since the $IC_{50}$; 191 values of these molecules are in the range 0.1 to 10.0 nm, these novel compounds are potentially useful for the treatment of CML.

40 Claims, 16 Drawing Sheets

Figure 3. The figure shows luciferase expression intensity of K562 luc cells implanted in nude mice followed by oral treatment of Imatinib.

PHENYLAMINOPYRIMIDINE DERIVATIVES AS INHIBITORS OF BCR-ABL KINASE

This application is a continuation-in-part of PCT/IN05/00243 filed Jul. 19, 2005.

The present invention relates to novel intermediates useful for the preparation of novel phenylaminopyrimidine derivatives, pharmaceutical composition containing the novel phenylaminopyrimidine derivatives and processes for their preparation. The invention particularly relates to novel Phenyl pyrimidine amine derivatives of the general formula I given below

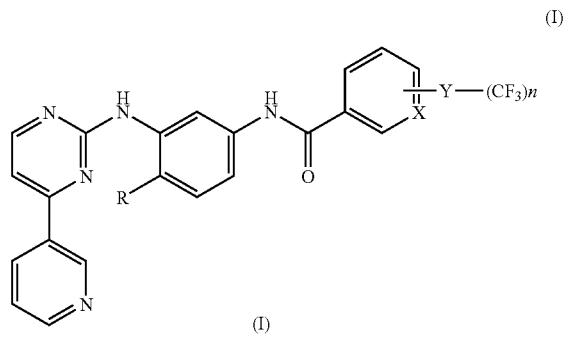

(I)

In the formula the symbols have the following meanings

| Series A | Series B |
|---|---|
| X = CH | X = N |
| n = 1, 2 | n = 1 |
| R = H, Me | R = H, Me |
| Y = 0(zero), S, SO, SO$_2$ | Y = 0(zero), S, SO, SO$_2$ |

The invention also provides the pharmaceutically acceptable salts of the formula I as defined above. Further, the present invention also provides a process for the preparation of the above said novel compounds and the pharmaceutically acceptable salts thereof. The invention also provides a pharmaceutical composition containing the novel compounds of the general formula I along with usually employed pharmaceutically acceptable excepients and a process for its preparation.

The novel compounds of the formula I can be used in the therapy of Chronic Myeloid Leukemia (CML). Since the IC$_{50}$ values of these molecules are in the range 0.1 to 10.0 nm, these novel compounds are potentially useful for the treatment of CML

BACKGROUND OF THE INVENTION

Phenyl pyrimidine amine derivatives are known from the patents WO 9509851, WO 9509853, EP0588762, WO 9509847, WO 9903854, and EP-B-0-564 409 as effective compounds for treatment of tumors.

For example in WO 9509851 compounds of the general formula II are disclosed

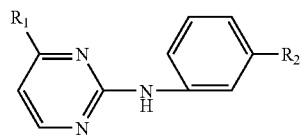

(II)

wherein
R1 is a substituted cyclic radical, the cyclic radical being bonded to a ring carbon atom in each case and being selected from phenyl, pyridyl, pyrazinyl, thiazolyl, pyrimidinyl, pyridazinyl and imidazolyl, and the substituents of the above-mentioned cyclic radical being selected from one or more of the groups halogen, cyano, carbamoyl, —C(=O)—OR3, —C(=O)—R4, —SO2-N(R5)-, —N(R7)-R8, —OR9 and fluorine substituted lower alkyl, wherein R3, R4, Rs, R6, R7, R8 and Rg are each independently of the others hydrogen or lower alkyl that is unsubstituted or substituted by mono- or di-lower alkylamino; and R2 is selected from halogen, cyano, carbamoyl, —C(=O)—OR10, —C(=O)—R11, —SO2-N(R12)-R13, —N(R14)-R15, —OR16 and fluorine-substituted lower alkyl, wherein R10, R11, R12, R13, R14, R1S and R16 are each independently of the others hydrogen or lower alkyl that is unsubstituted or substituted by mono- or di-lower alkylamino, or a salt of such a compound having at least one salt-forming group.

In WO 9509853, N-phenyl-2-pyrimidineamine derivative compounds of the general formula III are disclosed

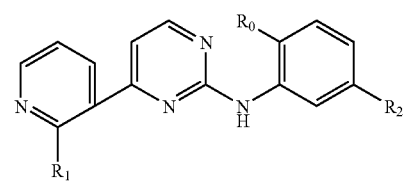

(III)

An N-phenyl-2-pyrimidineamine derivative of formula III wherein R0 is hydrogen, halogen, lower alkoxy or lower alkyl, R1 is
a) N-(amino-lower alkyl)-carbamoyl,
b) N-(hydroxy-lower alkyl)-carbamoyl,
c) hydrazino,
d) cyclohexyl-amino that is unsubstituted or substituted by amino,
e) piperazinyl that is unsubstituted or substituted by amino-lower alkyl,
f) morpholinyl, or
g) lower alkylamino that is substituted by morpholinyl, hydroxy-lower alkylamino, cyano, imidazolyl, guanidyl, amino, lower alkanoylamino, lower alkylamino-carbonylamino, amidino, di-lower alkylamino-cyclohexyl, carboxy, lower alkoxycarbonyl, carbamoyl, N-hydroxy-carbamoyl, hydroxy, lower alkoxy, dihydroxyphosphoryloxy, piperazinyl, lower alkanoyl-piperazinyl, formylpiperazinyl, prolylamido or by a radical of the formula H2 N—CH(R)—C (=O)—NH— wherein R is hydrogen, C1-C4 alkyl, benzyl, hydroxymethyl, 1-hydroxy-ethyl, mercaptomethyl, 2-methylthio-ethyl, indol-3-yl-methyl, phenyl-methyl, 4-hydroxy-phenyl-methyl, carbamoyl-methyl, 2-carbamoyl-ethyl, carboxy-methyl, 2-carboxy-ethyl, 4-amino-butyl, 3-guanidyl-propyl or R is 1H-imidazol-4-yl-methyl, and R2 is C1-C6 alkyl, C1-C3 alkoxy, chlorine, bromine, iodine, trifluoromethyl, hydroxy, phenyl, amino, mono(C1-C3 alkyl)amino, di(C1-C3 alkyl)amino, C2-C4 alkanoyl, propen-yloxy, carboxy, carboxy-methoxy, ethoxycarbonyl-methoxy, sulfanilamido, N,N-di-(C1-C3 alkyl) sulfanilamido, N-methyl-piperazinyl, piperidinyl, 1H-imidazol-1-yl, 1H-triazol-1-yl, 1H-benzimidazol-2-yl, 1-naphthyl, cyclopentyl, 3,4-dimethyl-benzyl or a radical of one of the formulae:

—CO2 R3, —NH—C(=O)—R3, —N(R3)-C(=O)—R4, —O—(CH2)n-N(R3)-R4, —C(.dbd.O)—NH—(CH2)n-R4@a, —C(=O)—NH—(CH2)n-N(R3)-R4, —CH(CH3)-NH—CHO, —C(CH3).dbd.N—OH, —C(CH3)=N—O—CH3, —CH(CH3)-NH2, —NH—CH2-C(=O)—N(R3)-R4, wherein R3 and R4 are each independently of the other C1-C3 alkyl, R4@a is hydroxy, amino or imidazolyl, X is oxygen or sulfur, m is 1, 2 or 3, n is 2 or 3, R5 is hydrogen, C1-C3 alkyl, C1-C3 alkoxy, chlorine, bromine, iodine or trifluoromethyl, R6 is 1H-imidazol-1-yl or morpholinyl and R7 is C1-C3 alkyl or is phenyl that is unsubstituted or mono-substituted by C1-C3 alkyl, halogen or by trifluoromethyl, or a salt thereof. An N-phenyl-2-pyrimidineamine derivative of formula III wherein R0 is hydrogen, halogen, lower alkoxy or lower alkyl, R1 is a) N-(amino-lower alkyl)-carbamoyl, b) N-(hydroxy-lower alkyl)-carbamoyl, c) hydrazino, d) cyclohexyl-amino that is unsubstituted or substituted by amino, e) piperazinyl that is unsubstituted or substituted by amino-lower alkyl, f) morpholinyl, or g) lower alkylamino that is substituted by morpholinyl, hydroxy-lower alkylamino, cyano, imidazolyl, guanidyl, amino, lower alkanoylamino, lower alkylamino-carbonylamino, amidino, di-lower alkylamino-cyclohexyl, carboxy, lower alkoxycarbonyl, carbamoyl, N-hydroxy-carbamoyl, hydroxy, lower alkoxy, dihydroxyphosphoryloxy, piperazinyl, lower alkanoyl-piperazinyl, formylpiperazinyl, prolylamido or by a radical of the formula H2 N—CH(R)—C(=O)—NH— wherein R is hydrogen, C1-C4 alkyl, benzyl, hydroxymethyl, 1-hydroxy-ethyl, mercaptomethyl, 2-methylthio-ethyl, indol-3-yl-methyl, phenyl-methyl, 4-hydroxy-phenyl-methyl, carbamoyl-methyl, 2-carbamoyl-ethyl, carboxy-methyl, 2-carboxy-ethyl, 4-amino-butyl, 3-guanidyl-propyl or R is 1H-imidazol-4-yl-methyl, and R2 is C1-C6 alkyl, C1-C3 alkoxy, chlorine, bromine, iodine, trifluoromethyl, hydroxy, phenyl, amino, mono(C1-C3 alkyl)amino, di(C1-C3 alkyl)amino, C2-C4 alkanoyl, propen-yloxy, carboxy, carboxy-methoxy, ethoxycarbonyl-methoxy, sulfanilamido, N,N-di-(C1-C3 alkyl)sulfanilamido, N-methyl-piperazinyl, piperidinyl, 1H-imidazol-1-yl, 1H-triazol-1-yl, 1H-benzimidazol-2-yl, 1-naphthyl, cyclopentyl, 3,4-dimethyl-benzyl or a radical of one of the formulae:

—CO2 R3, —NH—C(=O)—R3, —N(R3)-C(=O)—R4, —O—(CH2)n-N(R3)-R4, —C(=O)—NH—(CH2)n-R4@a, —C(=O)—NH—(CH2)n-N(R3)-R4, —CH(CH3)-NH—CHO, —C(CH3)=N—OH, —C(CH3)=N—O—CH3, —CH(CH3)-NH2, —NH—CH2-C(=O)—N(R3)-R4, wherein R3 and R4 are each independently of the other C1-C3 alkyl, R4@a is hydroxy, amino or imidazolyl, X is oxygen or sulfur, m is 1, 2 or 3, n is 2 or 3, R5 is hydrogen, C1-C3 alkyl, C1-C3 alkoxy, chlorine, bromine, iodine or trifluoromethyl, R6 is 1H-imidazol-1-yl or morpholinyl and R7 is C1-C3 alkyl or is phenyl that is unsubstituted or mono-substituted by C1-C3 alkyl, halogen or by trifluoromethyl, or a salt thereof.

EP0588762 eidem., U.S. Pat. No. 5,516,775 compounds of the general formula IV are disclosed

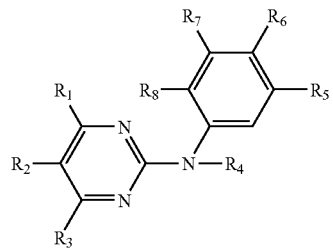

(IV)

wherein R1 is hydrogen or C1-C3 alkyl, R2 is hydrogen or C1-C3 alkyl, R3 is 2-pyridyl, 3-pyridyl, 4-pyridyl, 2-methyl-3-pyridyl, 4-methyl-3-pyridyl, 2-furyl, 5-methyl-2-furyl, 2,5-dimethyl-3-furyl, 2-thienyl, 3-thienyl, 5-methyl-2-thienyl, 2-phenothiazinyl, 4-pyrazinyl, 2-benzofuryl, N-oxido-2-pyridyl, N-oxido-3-pyridyl, N-oxido-4-pyridyl, 1H-indol-2-yl, 1H-indol-3-yl, 1-methyl-1H-pyrrol-2-yl, 4-quinolinyl, 1-methyl-pyridinium-4-yliodide, dimethylaminophenyl or N-acetyl-N-methylaminophenyl, R4 is hydrogen, C1-C3 alkyl, —CO—CO—O—C2 H5 or N,N-dimethylaminoethyl, at least one of R5, R6, R7 and R8 is C1-C6 alkyl, C1-C3 alkoxy, chloro, bromo, iodo, trifluoromethyl, hydroxy, phenyl, amino, mono-(C1-C3-alkyl) amino, di(C1-C3 alkyl)amino, C2-C4 alkanoyl, propenyloxy, carboxy, carboxymethoxy, ethoxycarbonylmethoxy, sulfanilamido, N,N-di(C1-C3 alkyl)sulfanilamido, N-methylpiperazinyl, piperidinyl, 1H-imidazol-1-yl, 1H-triazol-1-yl, 1H-benzimidazol-2-yl, 1-naphthyl, cyclopentyl, 3,4-dimethylbenzyl or a radical of one of the formulae:

—CO2 R, —NH—C(=O)—R, —N(R)—C(=O)—R, —O—(CH2)n-N(R)—R, —C(=O)—NH—(CH2)n-N(R)—R, —CH(CH3)-NH—CHO, —C(CH3)=N—OH, —C(CH3)=N—O—CH3, —C(CH3)-NH2, —NH—CH2-C(=O)—N(R)—R,

—(CH2)m-R10, —X—(CH2)m-R10 or wherein R is C1-C3 alkyl, X is oxygen or sulfur, m is 1, 2 or 3, n is 2 or 3, R9 is hydrogen, C1-C3 alkyl, C1-C3 alkoxy, chloro, bromo, iodo or trifluoromethyl, R10 is 1H-imidazol-1-yl or morpholinyl, and R11 is C1-C3 alkyl or unsubstituted phenyl or phenyl which is monosubstituted by C1-C3 alkyl, halogen or trifluoromethyl, and the other substituents R5, R6, R7 and R8 are hydrogen, or a pharmaceutically acceptable salt thereof.

In EP 0564 409 compounds of the general formula V are disclosed

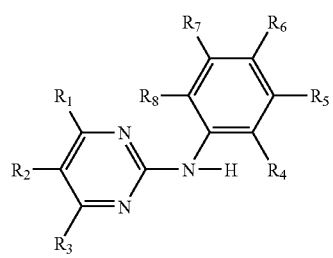

(V)

Wherein

R₁ is pyrazinyl, 1-methyl-1H-pyrrolyl, amino- or amino-lower alkyl-substituted phenyl wherein the amino group in each case is free, alkylated or acylated, 1H-indolyl or 1H-Imidazolyl bonded at a five-membered ring carbon atom, or unsubstituted or lower alkyl-substituted pyridyl bonded at a ring carbon atom and unsubstituted or substituted at the nitrogen atom by oxygen, R₂, R₃ are each independently of the other hydrogen or lower alkyl, one or two of the radicals R₄, R₅, R₆, R₇ and R₈ are each nitro, fluoro-substituted lower alkoxy or a radical of the formula (Va)

—N(R₉)—C(=X)—(Y)ₙ—R₁₀ (Va)

Wherein

R₉ is hydrogen or lower alkyl,

X is oxo, thio, imino, N-lower alkyl-imino, hydroximino or O-lower alkyl-hydroximino, Y is oxygen or the group NH, N is 0 or 1 and R₁₀ is an aliphatic radical having at least 5 carbon atoms, or an aromatic, aromatic-aliphatic, cycloaliphatic, cycloaliphatic-aliphatic, heterocyclic or hetero-cyclicaliphatic radical, And the remaining radicals R₄, R₅, R₆, R₇ and R₈ are each independently of the others hydrogen, lower alkyl that is unsubstituted or substituted by free or alkylated amino, piperazinyl, piperidinyl, pyrrolidinyl or by morpholinyl, or lower alkanoyl, trifluoromethyl, free, etherified or esterified hydroxyl, free, alkylated or acylated amino or free or esterified carboxy, or a salt of such a compound having at least one salt-forming group.

In WO 9509847, N-phenyl-2-pyrimidineamine derivative of the general formula VI are disclosed

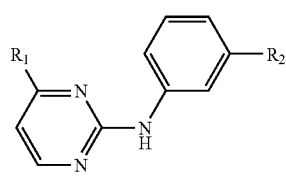

(VI)

wherein

R1 is naphthyl, fluorenyl, anthracenyl or a substituted cyclic radical, the cyclic radical being bonded to a ring carbon atom in each case and being selected from phenyl, pyridyl, 1H-indolyl, pyrazinyl, thiazolyl, pyrimidinyl, pyridazinyl and imidazolyl, and the substituents of the above-mentioned phenyl radical being selected from hydroxy, halogen, nitro, cyano, unsubstituted or halogen-substituted lower alkoxy, from a radical of formula VIa C(=O)—(O)m-R3 (V1a)

wherein m is 0 or 1 and

R3 is hydrogen, benzyl, lower alkyl or amino-lower alkyl wherein the amino group is free, lower alkylated or lower alkanoylated, from a radical of formula m —C(=O)—N(R4) R5 (V1b) wherein R4 and R5 are each independently of the other hydrogen or unsubstituted or amino- or hydroxy-substituted lower alkyl, from a radical of formula VIc —SO2-N(R6)R7 (VIc) wherein R6 and R7 are each independently of the other hydrogen, lower alkyl or amino-lower alkyl, or wherein R6 and R7 together form the bivalent radical —(CH2)2-NH—(CH2)2-, and from radical of formula VId —N(R8)R9 (VId) wherein R8 and R9 are each independently of the other lower alkyl, or wherein R8 is hydrogen and R9 is amino or amino-cyclohexyl, or is lower alkyl that is substituted by imidazolyl, guanidyl, lower alkylamino-carbonylamino, amidino, di-loweralkylamino-cyclohexyl, piperazinyl, carboxy, lower alkoxycarbonyl, carbamoyl, N-hydroxy-carbamoyl, hydroxy, lower alkoxy, dihydroxyphosphoryloxy or by formylpiperazinyl, and the substituents of the other above-mentioned cyclic radicals being selected from hydroxy, halogen, cyano, amino-lower alkyl, unsubstituted or halogen-substituted lower alkoxy, phthalimido-substituted lower alkyl, from a radical of the above-mentioned formulae VIa, m or VIc and from a radical of formula VII

—N(R10)R11 (VII)

wherein R10 and R11 are each independently of the other hydrogen or lower alkyl, or wherein R10 is hydrogen and R11 is amino or amino-cyclohexyl, or is lower alkyl substituted by amino, lower alkylamino, di-lower alkylamino, lower alkanoylamino, imidazolyl, guanidyl, lower alkylamino-carbonylamino, amidino, di-lower alkylamino-cyclohexyl, piperazinyl, formylpiperazinyl, carboxy, lower alkoxycarbonyl, carbamoyl, N-hydroxy-carbamoyl, hydroxy, lower alkoxy, dihydroxyphosphoryloxy or by glycylamido; and R2 is nitro, fluorine-substituted lower alkoxy or a radical of formula VIII —N(R12)-C(=X)—(Y)n-R13 (VIII)

wherein

R12 is hydrogen or lower alkyl,

X is oxo, thio, imino, N-lower alkyl-imino, hydroximino or O-lower alkyl-hydroximino, Y is oxygen or the group NH, n is O or 1, and R13 is an aliphatic radical having at least 5 carbon atoms, or an aromatic, aromaticaliphatic, cycloaliphatic, cycloaliphatic-aliphatic, heterocyclic or heterocyclic-aliphatic radical, or a salt of such a compound having at least one salt-forming group.

Furthermore EP0564409 discloses the use of said compounds in the treatment of artherosclerosis. The patent WO9903854 describes the use of pyridyl pyrimidine amine derivatives, especially of Gleevec™, the Novartis compound CGP57148 of the formula IX, as tyrosine kinase inhibitors in cancer treatment. The IC₅₀ value reported for Gleevec™, is 38 nano molars (nm).

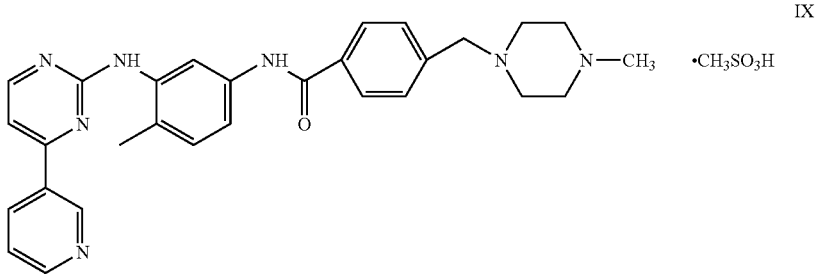

In the recent patent WO 0222597 dated Nov. 9, 2001 of Novartis, compounds of the formula (X) have been disclosed wherein:

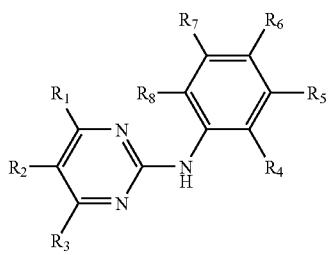

Ri is pyrazinyl; 1-methyl-1H-pyrrolyi; amino- or aminolower alkyl-substituted phenyl, wherein the amino group in each case is free, alkylated oracylated; 1H-indolyl or 1H-imidazolyl bonded at a five-membered ring carbon atom; or unsubstituted or lower alkyl substituted pyridyl bonded at a ring carbon atom and unsubstituted or substituted at the nitrogen atom by oxygen, R2 and R3 are each independently of the other hydrogen or lower alkyl, one of the radicals R4, R5, R6, R7 and R8 is a radical of formula 11 —N(R9)-C(=X)—(Y)n-R10 wherein Rg is hydrogen or lower alkyl, X is oxo, thio, imino, N-lower alkyl-imino, hydroximino or 0-lower alkyl-hydroximino, Y is oxygen or the group NH, n is 0 or 1 and R10 is phenyl which is a) substituted by a radical selected from the group consisting of amino; mono- or di lower alkylamin; lower alkanoylamino; formyl; lower alkoxy-carbonyl; and lower alkyl which is substituted by amino, mono- or di-lower alkylamin or loweralkanoylamino, or b) substituted by an unsubstituted or substituted radical selected from the group consisting of benzylamino; benzoylamino; pyrrolidinyl; piperidyl; piperazinyl; piperazinyl-carbonyl; morpholinyl; and lower alkyl substituted by benzylamino, benzoylamino, pyrrolidinyl, piperidyl, piperazinyl or morpholinyl, the substituents of said substituted radical being selected from the group consisting of cyano; lower alkyl; hydroxy- or amino-substituted lower alkyl; trifluoromethyl; hydroxy; lower alkoxy; lower alkanoyloxy; amino; mono- or di-lower alkylamin; lower alkanoylamino; benzoylamino; carboxy; lower alkoxycarbonyl and halogen, and c) optionally further substituted by one or more radicals selected from the group consisting of cyano; lower alkyl; hydroxy- or amino-substituted lower alkyl; trifluoromethyl; hydroxy; lower alkoxy; lower alkanoyloxy; amino; mono- or di-lower alkylamin; lower alkanoylamino; benzoylamino; carboxy; lower alkoxycarbonyl and halogen, with the proviso that RIO is not (4-methyl-piperazinyl)-methylphenyl, and the remaining radicals R4, R5, R6, R7 and R8 are each independently of the others hydrogen; lower alkyl that is unsubstituted or substituted by free or alkylated amino, piperazinyl, piperidyl, pyrrolidinyl or morpholinyl; lower alkanol; trifluoromethyl; free, etherified or esterified hydroxy; free, alkylated oracylated amino; or free or esterified carboxy, or a salt of such a compound having at least one salt-forming group.

It is very well known that phenyl amino pyrido pyrimidines falling under the above mentioned categories are found to be very useful for the treatment of Bcr-abl positive cancer and tumor diseases, such as leukemias [especially Chronic Myeloid Leukemia (CML) and Acute Lymphoblastic Leukemia, where especially apoptotic mechanisms of action are found]. Consequently interest and attention are being given for developing more new molecules falling within above mentioned categories of compounds.

With the above objectives in view we continued our R & D in the above mentioned directions and have filed applications for patents both for new molecules as well as for the improved processes for the preparation of such molecules Therefore, the main objective of the present invention is to provide novel phenyl amino pyrido pyrimidines of general formula (I) defined above and their pharmaceutically acceptable salts Another objective of the present invention is to provide novel phenyl amino pyrido pyrimidines of general formula (I) defined above and their pharmaceutically acceptable salts which have $IC_{50}$ values in the range 0.1 to 10.0 nm Yet another objective of the present invention is to provide novel phenyl amino pyrido pyrimidines of general formula (I) and their pharmaceutically acceptable salts which are useful for the treatment of CML Still another objective of the present invention is to provide a process for the preparation of novel phenyl amino pyrido pyrimidines of general formula (I) defined above and their pharmaceutically acceptable salts Further objective of the present invention is to provide a pharmaceutical composition containing the novel phenyl amino pyrido pyrimidines of general formula (I) and their pharmaceutically acceptable salts useful for the treatment of CML Still another objective of the present invention is to provide a process for the preparation of pharmaceutical composition containing novel phenyl amino pyrido pyrimidines of general formula (I) defined above and their pharmaceutically acceptable salts Still another objective of the present invention is to provide novel intermediates useful for the preparation of novel compounds of the formula I defined above Yet another objective of the present invention is to provide processes for the preparation of novel intermediates useful for the preparation of novel compounds of the formula I defined above

Figure 1:
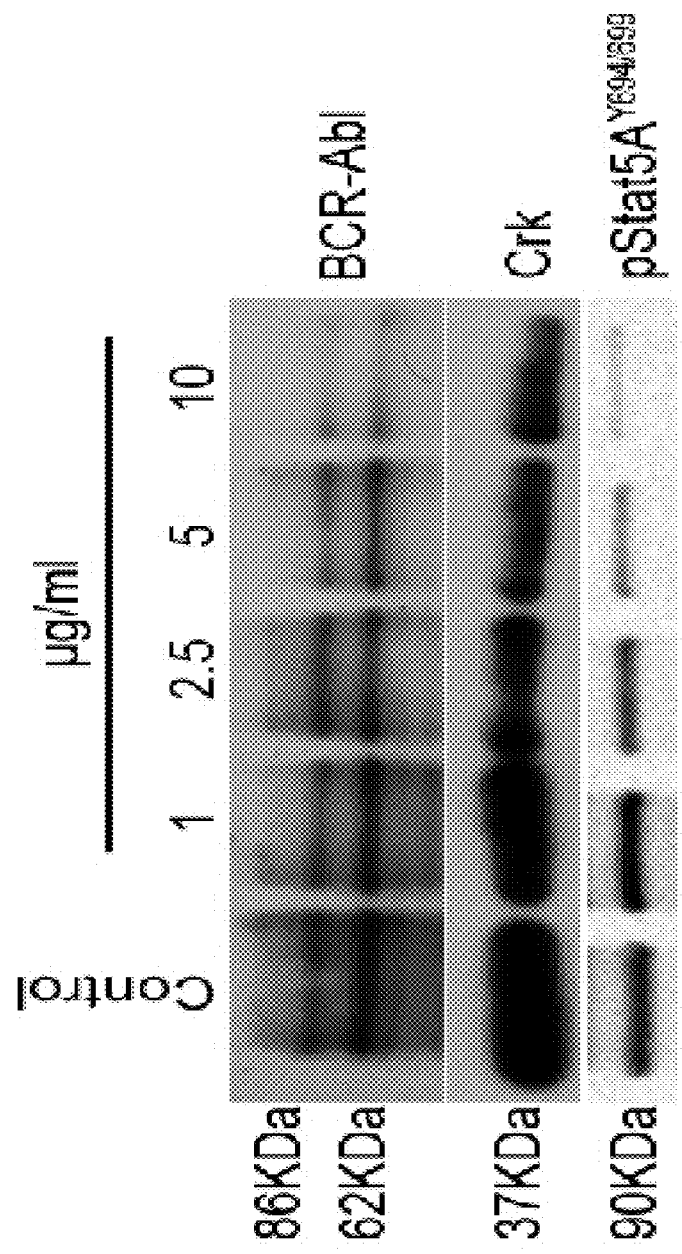
FIG. 1—D32p210 cells were grown in RPMI medium supplemented with 10% FBS in humidified air at 5% $CO_2$ and 37° C. For MTT assay, 5×10³ cells/well were seeded in a 96-well plate and required drug (AN015) concentration ranging from 1 nM to 10 □M was added incubated fro 24 hrs. Cell proliferation was assessed by incubating the cells with 20 □l of MTT (5 mg/ml stock) for additional 3 hrs followed by addition of lysis buffer to dissolve the formazan crystals. After overnight incubation, the absorbance was recorded using ELISA reader at a dual wavelength of 570-630 nm. After a serious of such experiments, a narrower range of concentrations (5 nM to 10 nM) was selected and MTT assay was repeated to determiner the $IC_{50}$ value.

Accordingly, the present invention provides phenyl amino pyrido pyrimidines of general formula (I)

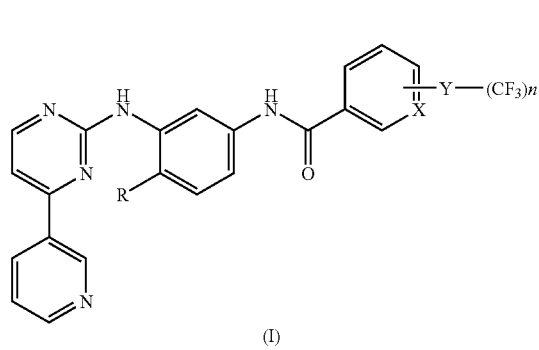

(I)

Wherein the symbols have the following meanings

| Series A | Series B |
|---|---|
| X = CH | X = N |
| n = 1, 2 | n = 1 |
| R = H, Me | R = H, Me |
| Y = 0(zero), S, SO, $SO_2$ | Y = 0(zero), S, SO, $SO_2$ | and the pharmaceutically acceptable salts thereof

The trifluoro methyl group in the above compounds is preferably bonded to the phenyl/pyridinyl at position 3 (when n=1) and when two such groups are present, they are preferably bonded at positions 3,5 (when n=2)

Special preference is given to compounds of the general formula (I) wherein R represents methyl group and the trifluoromethyl group is present in position 3 of the phenyl/pyridinyl ring (n=1, Series-A, Series-B) and when two such groups are present, bonding at position 3,5- is preferred (n=2, Series-A).

Very special preference is given to compound(s) of general formula (I) where in R represents a methyl group and the trifluoromethyl group is present in position 3 and position 3,5- of the phenyl ring (n=1; and 2, Series-A)

The above mentioned compounds are new as they have not been reported in the literature The compounds of the formula (I) form pharmaceutically acceptable salts. For example salts are formed with inorganic acids such as hydrochloric acid, sulfuric acid, phosphoric acid, (or) with suitable organic carboxylic (or) sulfonic acids for example aliphatic mono- (or) dicarboxylic acids, such as trifluoro acetic acid acetic acid, propionic acid, glycolic acid, succinic acid, maleic acid, fumaric acid, hydroxymaleic acid, malic acid, tartaric acid citric acid (or) oxalic acid (or) amino acids such as arginine (or) lysine, aromatic carboxylic acids, such as benzoic acid, 2-phenoxy benzoic acid, 2-acetoxy benzoic acid, salicylic acid aromatic aliphatic carboxylic acids, such as nicotinic acid aliphatic sulfonic acids, such as methane sulfonic acid and aromatic sulfonic acids like for example benzene and 4-toluene sulfonic acids.

However, only pharmaceutically acceptable non toxic salts are used for the therapeutic purposes, and those salts are therefore preferred.

According to another embodiment of the invention there is provided a process for the preparation of novel phenyl amino pyrido pyrimidines of the formula I,

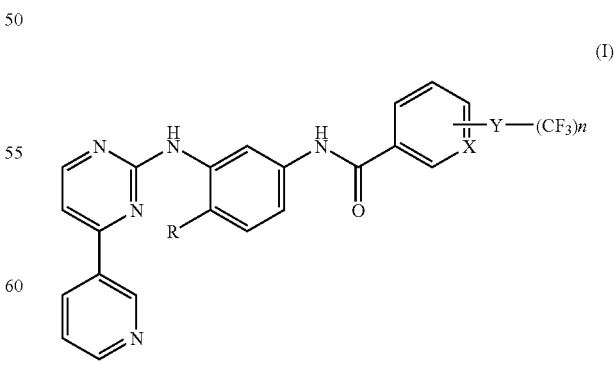

(I)

where the symbols have the meanings given below and their pharmaceutically acceptable acid addition salts which comprises (i) condensing 4-methyl-3-nitroaniline of the formula (XI)

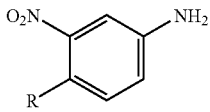
(XI)

wherein R represents hydrogen or methyl with trifluoro methyl aroyl chlorides of the formula (XII),

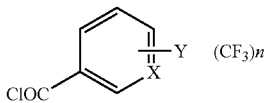
(XII)

n represents 1 or 2 and x represents N or H in the presence of chloro hydrocarbon solvent and a base at a temperature in the range of 30 to 40 Deg C. to yield the novel intermediate nitro trifluoromethyl aroyl amides of the formula (XIII)

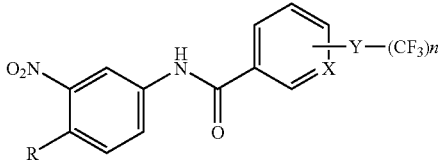
(XIII)

where R and n have the meanings given above (ii) Reducing the resulting novel compounds of the formula (XIII) using a metal—acid reducing agent at a temperature in the range of 0-5° C. to yield the novel intermediate amino trifluoromethyl aroyl amides of the formula (XIV)

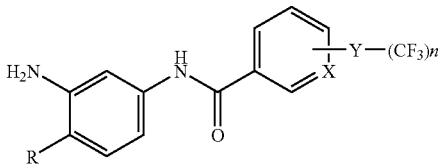
(XIV)

where R & n have the meanings given above.

(iii) condensing the compounds of the formula (XIV) with cyanamide ($CNNH_2$) at a temperature in the range of 60 to 95° C. in the presence of polar solvent and an inorganic acid to yield the novel intermediate salts of guanidino trifluoromethyl aroyl amides of formula (XV)

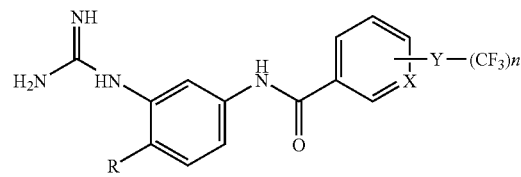
(XV)

where R and n have the meanings given above and (iv) condensing the novel compounds of the formula (XV) with a compound of formula (XVI) in the presence of a base and at a temperature in the range of 30 to 40 Deg C. to yield the novel compounds of general formula (I) where R, n, X are as defined above and if desired converting the novel compounds of the formula I into pharmaceutically acceptable salts by conventional methods The above defined process is shown in the Scheme I given below Scheme I:

Step-i:

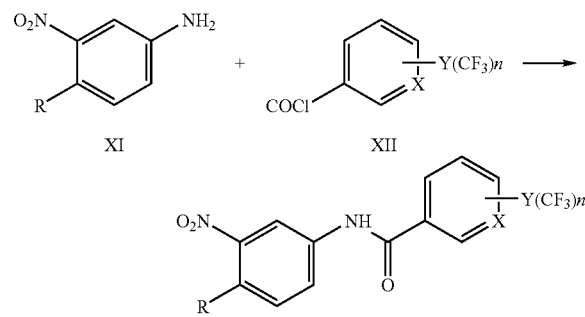

Step-ii:

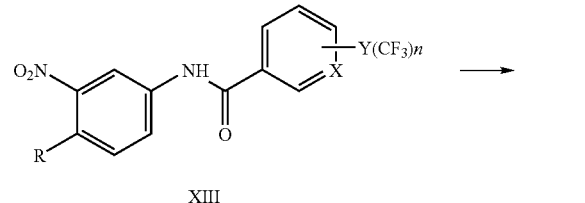

Step-iii:

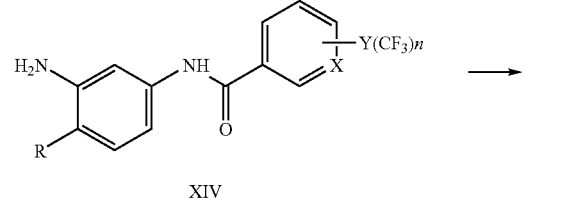

-continued

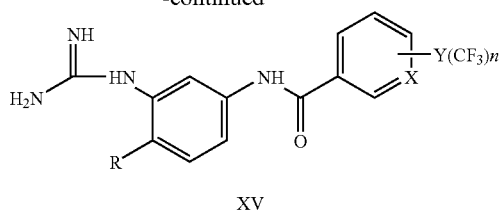
XV

Step-iv:

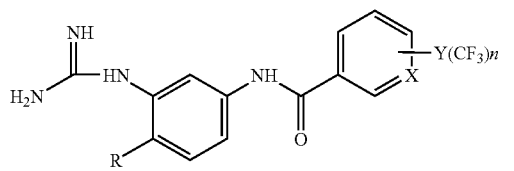
XV

+

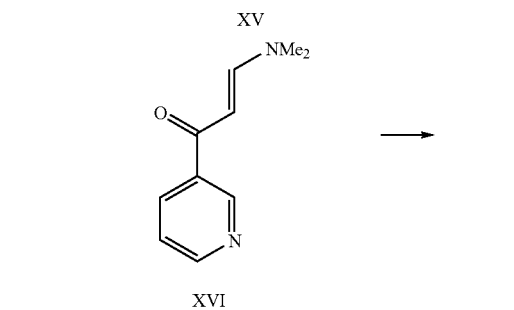
XVI

→

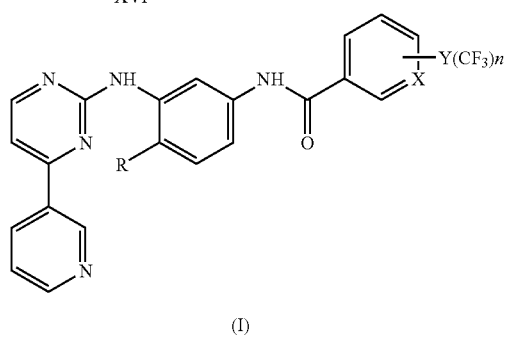
(I)

According to another embodiment of the invention there is provided a process for the preparation of novel nitro trifluoromethyl aroyl amides of the formula (XIII)

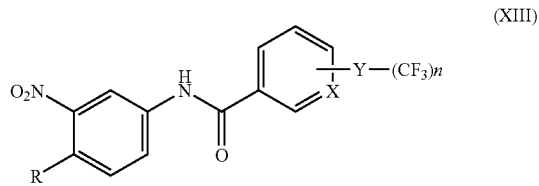
(XIII)

Useful as an intermediate for the preparation of novel compound of the formula I which comprises condensing 4-methyl-3-nitroaniline of the formula (XI)

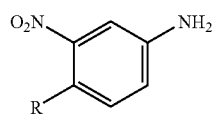
XI wherein R represents hydrogen or methyl with trifluoro methyl aroyl chlorides of the formula (XII),

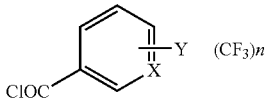
(XII)

wherein n represents 1 or 2 and x represents N or H in the presence of chloro hydrocarbon solvent and a base at a temperature in the range of 30 to 40 Deg C. to yield the novel intermediate nitro trifluoromethyl aroyl amides of the formula (XIII)

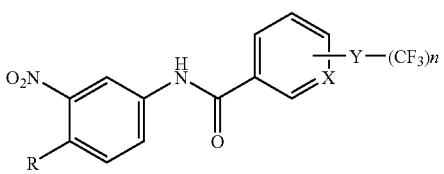
(XIII)

According to another embodiment of the invention there is provided a process for the preparation of novel amino trifluoromethyl aroyl amides of the formula (XIV)

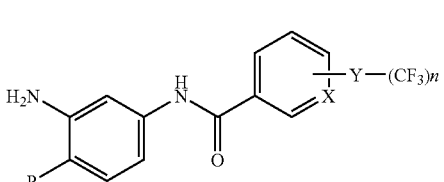
(XIV)

where R & n have the meanings given above.

useful for the preparation of novel compounds of the formula I which comprises reducing the r novel compounds of the formula (XIII) using a metal-acid reducing agent at a temperature in the range of 0-5° C. to yield the novel compounds of the formula XIV According to another embodiment of the invention there is provided a process for the preparation of novel salts of guanidino trifluoromethyl aroyl amides of formula (XV)

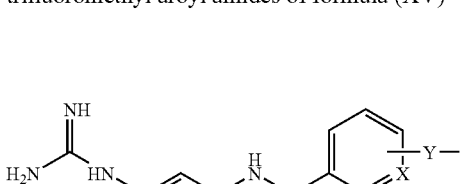
(XV)

where R and n have the meanings given above, useful as an intermediate for the preparation of new compounds of the formula I which comprises condensing the compounds of the formula (XIV) with cyanamide ($CNNH_2$) at a temperature in the range of 60 to 95° C. in the presence of polar solvent and an inorganic acid to yield the novel intermediate of formula (XV)

In a preferred embodiment of the invention, the chloro hydrocarbon solvent used in step (i) may be selected from—Chloroform, Methylene chloride or ethylene chloride, preferably chloroform The base used may be selected from triethyl amine, dipropyl amine or diisopropyl amine preferably triethyl amine. The temperature may be preferably in the range of 30 to 40-Deg C.

In another embodiment the metal—acid reducing agent used in step (ii) for reducing the novel compound of the formula-XII may be selected from stannous chloride/Concd. HCl iron/Concd. HCl, Zinc-Concd. HCl, preferably stannous chloride/Concd. HCl The polar solvent used in step (iii) may be selected from n-propanol, isopropanol, ethanol, n-butanol or their mixtures preferably n-butanol.

The base such as potassium hydroxide or sodium hydroxide preferably may be used in step (iv) and the temperature may be at the range of 90-95 deg C.

According to yet another embodiment of the present invention there is provided an alternative process for the preparation of the compounds of the general formula I as defined above Accordingly the present invention provides a process for the preparation of compounds of the general formula I as defined above which comprises (i) Preparing N-(5-amino-2-methylphenyl)-4-(3-pyridyl)-2-pyrimidine amine of the formula (XVII)

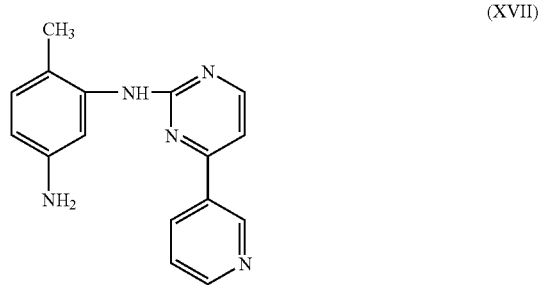

(XVII)

by conventional methods.

(ii) Condensing N-(5-amino-2-methylphenyl)-4-(3-pyridyl)-2-pyrimidine amine of the formula (XVII) with trifluoro methyl aroyl chlorides of the formula (XII) to yield the novel compounds of general formula (I) where [Y, n, X are as defined above]

The compounds of the formula (I) as defined above inhibit Bcr-abl Kinase and are thus, as explained above, suitable for the treatment of Bcr-abl positive cancer and tumor diseases, such as leukemias (especially Chronic Myeloid Leukemia (CML) and Acute Lymphoblastic Leukemia, where especially apoptotic mechanisms of action are found)

The invention also relates to pharmaceutical compositions comprising an affective amount, especially an amount effective in the prevention or therapy of one of the abovementioned diseases, of the active ingredient together with pharmaceutically acceptable carriers that are suitable for topical, enteral, for example oral or rectal, or parental administration, and may be inorganic or organic, solid or liquid. In addition to the active ingredient(s), the pharmaceutical compositions of the present invention may contain one or more excipients or adjuvants. Selection of excipients and the amounts to use may be readily determined by the formulation scientist based upon experience and consideration of standard procedures and reference works in the field.

Diluents increase the bulk of a solid pharmaceutical composition, and may make a pharmaceutical dosage form containing the composition easier for the patient and care giver to handle. Diluents for solid compositions include, for example, microcrystalline cellulose (e.g. Avicel(R)), microfine cellulose, lactose, starch, pregelitinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g. Eudragit(R)), potassium chloride, powdered cellulose, sodium chloride, sorbitol and talc.

Solid pharmaceutical compositions that are compacted into a dosage form, such as capsules may include excipients whose functions include helping to bind the active ingredient and other excipients together after compression. Binders for solid pharmaceutical compositions include acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. Klucel(R)), hydroxypropyl methyl cellulose (e.g. Methocel(R)), liquid glucose, magnesium aluminum silicate, maltodextrin, methylcellulose, polymethacrylates, povidone (e.g. Kollidon(R), Plasdone(R)), pregelatinized starch, sodium alginate and starch.

The dissolution rate of a compacted solid pharmaceutical composition in the patient's stomach may be increased by the addition of a disintegrant to the composition. Disintegrants include alginic acid, carboxymethylcellulose calcium, carboxymethylcellulose sodium (e.g. Ac-Di-Sol(R), Primellose (R)), colloidal silicon dioxide, croscarmellose sodium, crospovidone (e.g. Kollidon(R), Polyplasdone(R)), guar gum, magnesium aluminum silicate, methyl cellulose, microcrystalline cellulose, polacrilin potassium, powdered cellulose, pregelatinized starch, sodium alginate, sodium starch glycolate (e.g. Explotab(R)) and starch.

Glidants can be added to improve the flowability of a non-compacted solid composition and to improve the accuracy of dosing. Excipients that may function as glidants include colloidal silicon dixoide, magnesium trisilicate, powdered cellulose, starch, talc and tribasic calcium phosphate.

When a dosage form such as a capsule is made by the compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition to reduce adhesion and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc and zinc stearate.

Flavoring agents and flavor enhancers make the dosage form more palatable to the patient. Common flavoring agents and flavor enhancers for pharmaceutical products that may be included in the composition of the present invention include maltol, vanillin, ethyl vanillin, menthol, citric acid, fumaric acid, ethyl maltol, and tartaric acid.

Solid compositions may also be dyed using any pharmaceutically acceptable colorant to improve their appearance and/or facilitate patient identification The details of the invention are provided in the Examples given below which are provided to illustrate the invention only and therefore they should not be construed to limit the scope of the invention

EXAMPLE-1

Preparation of (3-trifluoromethyl)-N-[4-methyl-3-(4-pyridin-3-yl-pyrimidin-2-ylamino)-phenyl]-benzamide of the formula (I) where R represents methyl, X represents CH, Y represents zero and n=1:

Step I: Preparation of novel (3-trifluoromethyl)-N-(4-methyl-3-nitro-phenyl)-benzamide of the formula (XIII) where R represents methyl, X represents CH, Y represents zero and n=1

In the first instance, 3-trifluoro methyl benzoyl chloride which is used as one of the starting material is prepared as follows.

Thionyl chloride (312.0 g, 2.63 mol) is added over a period of 15 min to a solution of 3-trifluoro methyl benzoic acid (100.0 g, 0.53 mol) in chloroform (1000 ml) at room temperature. The reaction mixture is heated to reflux temperature for 1 hour. The excess of thionyl chloride is removed by co-distillation with chloroform under reduced pressure at 40° C. After the end of the distillation, the resulting trifluoro methyl benzoyl chloride is cooled down to room temperature and dissolved in 100 ml chloroform.

A solution of 4-methyl-3-nitroaniline (49.0 g, 0.32 mol) in chloroform (600 ml) is cooled to −5° C. and triethyl amine (161.0 g, 1.59 mol) of is added. Trifluoromethyl benzoyl chloride in chloroform prepared as described above is added drop wise at −5° C. over a period of 60-75 min. The resulting suspension is stirred for 1 hr at −5° C. The suspension is distilled to a residual volume of 800 ml and filtered, washed with chilled chloroform (250 ml) and dried in vacuum to give 85.0 g of novel (3-trifluoromethyl)-N-(4-methyl-3-nitro-phenyl)-benzamide of the formula (IV) where R represents methyl, X represents CH and n=1 (83%) as pale yellow crystals (98.0% purity by HPLC) MR-162-164° C.

Step II: Preparation of novel (3-trifluoromethyl)-N-(3-amino-4-methyl-phenyl)-benzamide of the formula (XIV) where R represents methyl, X represents CH, Y represents zero and n=1

A suspension of (3-trifluoromethyl)-N-(4-methyl-3-nitrophenyl)-benzamide of the formula (XIII) (85 g, 0.26 moles) prepared by the process described in step I and stannous chloride (297.5 g, 1.3 moles) in absolute ethanol (490 ml) is heated to reflux temperature for 30 min. The resulting suspension is then cooled to room temperature and quenched into 4 L of ice cold water. The reaction mixture $P^H$ is adjusted to 8.0 with 2.4 L of 5% sodium hydroxide solution and extracted with 2×2 L of ethyl acetate. The ethyl acetate layer is washed successively with water and brine and dried over sodium sulfate. The ethyl acetate is distilled completely and 500 ml of hexane is added to the residue and filtered. The filtered cake is dried in vacuum at 60° C. to give 60.0 g of novel (3-trifluoromethyl)-N-(3-amino-4-methyl-phenyl)-benzamide of the formula (XIV) where R represents methyl, X represents CH and n=1 (80%) as yellow crystals (98.2% purity by HPLC) MR-145-149° C.

Step III: Preparation of—(3-trifluoromethyl)-N-(3-guanidino-4-methyl-phenyl))-benzamide of the formula (XV) where R represents methyl, X represents CH, Y represents zero and n=1

A suspension of (3-trifluoromethyl)-N-(3-amino-4-methyl-phenyl)-benzamide of the formula (XIV) prepared by the process described in step (II) (60 g, 0.20 mol) in n-butanol (400 ml) is treated sequentially with concentrated nitric acid until the pH reaches 2.5 (13 g) and with a solution of cyanamide (12.6 g, 0.3 mol) in water (13 ml) over a period of 30 min. The resulting reaction mixture is stirred at reflux temperature for 6 hrs. The reaction mixture is then distilled off completely under vacuum and the residue is allowed to cool down to room temperature. A mixture of 240 ml of methanol and 240 ml of IPE is added to the reaction mass and stirred at room temperature for 1 hr. The product is filtered off with suction, washed with a mixture of methanol and IPE (3×50 ml) and dried in vacuum at 60° C. to give 43.2 g of the nitrate salt of (3-trifluoromethyl)-N-(3-guanidino-4-methyl-phenyl))-benzamide of the formula (XV), where R represents methyl, X represents CH and n=1 53% of theory (99% area by HPLC) MR-243-245° C.

Step (IV): Preparation of (3-trifluoromethyl)-N-[4-methyl-3-(4-pyridin-3-yl-pyrimidin-2-ylamino)-phenyl]-benzamide of the formula (I) where R represents methyl, X represents CH, Y represents zero and n=1

A suspension of nitrate salt of (3-trifluoromethyl)-N-(3-guanidino-4-methyl-phenyl)-benzamide nitrate prepared by the process described in step (XV) (43 g, 0.11 mol) in n-butanol (290 ml) under an atmosphere of nitrogen is treated successively with sodium hydroxide flakes (6.9 g, 0.17 mol) and 3-dimethylamino-1-pyridin-3-yl-propenone (18.6 g, 0.11 mol). The resulting suspension is heated to reflux temperature for 2 hrs. The reaction mixture becomes a homogeneous deep orange solution and dimethylamine is removed by the distillation of n-butanol. Reaction mass is cooled down to RT and a mixture of water and chloroform (250 ml+250 ml) is added and chloroform layer is separated out. The chloroform layer is washed with water and distilled to a residual volume of 40 ml. Ethyl acetate (200 ml) is added to the reaction mass and filtered off with suction, the isolated solid is washed with ethyl acetate (2×50 ml) and water (2×50 ml) and dried in vacuum at 60° C. Yield: 29.0 g of novel (3-trifluoromethyl)-N-[4-methyl-3-(4-pyridin-3-yl-pyrimidin-2-ylamino)-phenyl]-benzamide of the formula (I) where R represents methyl, X represents CH and n=1 60% based on theory, as pale yellow crystals.

(99.89% purity by HPLC). MR-211-213° C.
$IC_{50}$-8 nms (FIG. 1)
$^1$H-NMR (400 MHz, DMSO-$d_6$, δ):
2.23 (s, 3H); 7.20-9.28 (Aryl, 13H); 10.42 (s, 1H)

| Analysis | $C_{24}H_{18}F_3N_5O$ |
|---|---|
| Molecular weight | 449.0 |
| IR | KBR Disc |
| —NH—C=O | at 3445 cm$^{-1}$ |
| —NH—C=O | At 1648 cm$^{-1}$ |

EXAMPLE-2

Alternative process for the Preparation of (3-trifluoromethyl)-N-[4-methyl-3-(4-pyridin-3-yl-pyrimidin-2-ylamino)-phenyl]-benzamide of the formula (I) where R represents methyl, X represents CH, Y represents zero and n=1

In the first instance, 3-Trifluoro methyl benzoyl chloride which is used as one of the starting material is prepared as follows.

Thionyl chloride (2.65 kg, 3.72 mol) is added over a period of 15 min to a solution of 3-trifluoro methyl benzoic acid (0.848 kg, 4.46 mol) and D.M.F. (8.5 ml) in chloroform (9 L) at room temperature. The reaction mixture is heated to reflux temperature for 1 hour.

The excess of thionyl chloride is removed by co-distillation with chloroform under reduced pressure at 40° C. After the end of the distillation, the resulting 3-trifluoro methyl benzoyl chloride is cooled down to room temperature and dissolved in 600 ml chloroform.

A solution of N-(5-amino-2-methylphenyl)-4-(3-pyridyl)-2-pyrimidine amine of the formula (XVII) (1.03 kgs, 3.72 mol) in chloroform (9 L) is cooled to −5° C. and triethyl amine (1.35 kg, 13.37 mol) is added. Trifluoromethyl benzoyl chloride in chloroform prepared as described above is added drop wise at −5° C. over a period of 60-75 min. The resulting suspension is stirred for 1 hr at −5° C. The suspension is distilled to a residual volume of 6 L and filtered, washed with D.M. water and methanol (2.5 L) and dried in vacuum to give 1 kg of novel (3-trifluoromethyl)-N-[4-methyl-3-(4-pyridin-3-yl-pyrimidin-2-ylamino)-phenyl]-benzamide of the formula (I) where R represents methyl, X represents CH and n=1 (60%) as pale yellow crystals (95.0% area by HPLC). This product is further purified by refluxing with 3 volumes of ethylacetate and filtering at 40° C. [0.85 kg, 50.9%] (98.5% purity by HPLC) MR-MR-210-213° C.

EXAMPLE-3

Preparation of (3,5-Bis trifluoromethyl)-N-[4-methyl-3-(4-pyridin-3-yl-pyrimidin-2-ylamino)-phenyl]-benzamide(I) where R represents methyl, X represents CH, Y represents zero and n=2

Step I: Preparation of novel (3,5-Bis trifluoromethyl)-N-(4-methyl-3-nitro-phenyl)-)-benzamide (XIII) where R represents methyl, X represents CH, Y represents zero and n=2

In the first instance, 3,5-Bis trifluoro methyl benzoyl chloride which is used as one of the starting materials is prepared as follows.

Thionyl chloride (576.0 g, 4.8 mol) is added over a period of 15 min to a solution of 3,5-Bis trifluoro methyl benzoic acid (Lancaster) (250.0 g, 0.97 mol) in chloroform (2.5 L) at room temperature. The reaction mixture is heated to reflux temperature for 1 hour. The excess of thionyl chloride is removed by co-distillation with chloroform under reduced pressure at 40° C. After the end of the distillation, the resulting 3,5-Bis trifluoro methyl benzoyl chloride is cooled down to room temperature and dissolved in 400 ml chloroform. A solution of 4-methyl-3-nitroaniline (92.0 g, 0.60 mol) in chloroform (1.2 L) is cooled to −5° C. and triethyl amine (304.8 g, 3.0 mol) of is added. 3,5-Bis trifluoro methyl benzoyl chloride in chloroform is added drop wise at −5° C. over a period of 60-75 min. The resulting suspension is stirred for 1 hr at −5° C. The suspension is distilled to a residual volume of 800 ml and filtered, washed with chilled chloroform (200 ml) and dried in vacuum to give 160.0 g of novel (3,5-Bis trifluoromethyl)-N-(4-methyl-3-nitro-phenyl)-)-benzamide (XIII) where R represents methyl, X represents CH and n=2 (68%) as cream colored crystals (98.2% purity by HPLC) MR-123-130° C.

Step (II): Preparation of (3,5-Bis trifluoromethyl)-N-(3-amino-4-methyl-phenyl)-)-benzamide (XIV) where R represents methyl, X represents CH, Y represents zero and n=2

A suspension of novel (3,5-Bis trifluoromethyl)-N-(4-methyl-3-nitro-phenyl)-benzamide (XIII) (160 g, 0.41 moles) and stannous chloride (460.8 g, 2.0 moles) in absolute ethanol (850 ml) is heated to reflux temperature for 40 min. The resulting suspension is then cooled to room temperature and quenched into 5 L of ice cold water. The reaction mixture $P^H$ is adjusted to 8.0 with 4.3 L of 5% sodium hydroxide solution and extracted with 2×2 L of ethyl acetate. The ethyl acetate layer is washed successively with water and brine and dried over sodium sulfate. The ethyl acetate is distilled completely and 500 ml of hexane is added to the residue and filtered. The filtered cake is dried in vacuum at 60° C. to give 96.0 g of novel (3,5-Bis trifluoromethyl)-N-(3-amino-4-methyl-phenyl)-)-benzamide (XIV) where R represents methyl, X represents CH and n=2 of the formula (V) (65%) as yellow crystals.

(98.5% purity by HPLC) MR-153-156° C.

Step (III): Preparation of (3,5-Bis-trifluoromethyl)-N-(3-guanidino-4-methyl-phenyl)-benzamide (XV) where R represents methyl, X represents CH, Y represents zero and n=2

A suspension of (3,5-Bis-trifluoromethyl)-N-(3-amino-4-methyl-phenyl)-benzamide (90 g, 0.20 mol) in n-butanol (500 ml) is treated sequentially with concentrated nitric acid until the pH reaches 2.5 (15.9 g) and with a solution of cyanamide (15.7 g, 0.37 mol) in water (15 ml) over a period of 30 min. The resulting reaction mixture is stirred at reflux temperature for 6 hrs. The reaction mixture is then distilled off completely under vacuum and the residue is allowed to cool down to room temperature. A mixture of 180 ml of methanol and 180 ml of IPE is added to the reaction mass and stirred at room temperature for 1 hr. The product is filtered off with suction, washed with a mixture of methanol and IPE (3×50 ml) and dried in vacuum at 60° C. to give 72.0 g of the nitrate salt of novel (3,5-Bis-trifluoromethyl)-N-(3-guanidino-4-methyl-phenyl)-benzamide of the formula (XV) where R represents methyl, X represents CH and n=2 62% of theory (99.2% purity by HPLC), MR-285-287° C.

Step (IV): Preparation of (3,5-Bis trifluoromethyl)-N-[4-methyl-3-(4-pyridin-3-yl-pyrimidin-2-ylamino)-phenyl]-benzamide(I) where R represents methyl, X represents CH, Y represents zero and n=2

A suspension of (3,5-Bis-trifluoromethyl)-N-(3-guanidino-4-methyl-phenyl)-benzamide nitrate (70 g, 0.15 mol) in n-butanol (470 ml) under an atmosphere of nitrogen is treated successively with sodium hydroxide flakes (7.0 g, 0.18 mol) and 3-dimethylamino-1-pyridin-3-yl-propenone (28.0 g, 0.16 mol). The resulting suspension is heated to reflux temperature for 2 hrs. The reaction mixtures becomes a homogeneous deep orange solution and dimethylamine is removed by the distillation of n-butanol. Reaction mass is cooled down to RT and a mixture of water and chloroform (300 ml+300 ml) is added and chloroform layer is separated out. The chloroform layer is washed with water and distilled to a residual volume of 70 ml. Ethyl acetate (350 ml) is added to the reaction mass and filtered off with suction, the isolated solid is washed with ethyl acetate (2×50 ml) and water (2×50 ml) and dried in vacuum at 60° C. Yield: 48.0 g of (3,5-Bis trifluoromethyl)-N-[4-methyl-3-(4-pyridin-3-yl-pyrimidin-2-ylamino)-phenyl]-benzamide of the formula I where R represents methyl, X represents CH and n=2 62% based on theory, as pale yellow crystals. (99.9% purity by HPLC)

MR-248-250° C., $IC_{50}$-0.7 nms (FIG. 2)
$^1$H-NMR (400 MHz, DMSO-$d_6$, δ):
2.24 (s, 3H); 7.22-9.28 (Aryl, 12H); 10.61 (s, 1H)

| Analysis | $C_{25}H_{17}F_6N_5O$ |
|---|---|
| Molecular weight | 517.0 |
| IR | KBR Disc |
| —NH—C=O | at 3445.3 cm$^{-1}$ |
| —NH—C=O | At 1651.6 cm$^{-1}$ |

EXAMPLE-4

Alternative process for the Preparation of (3,5-Bis trifluoromethyl)-N-[4-methyl-3-(4-pyridin-3-yl-pyrimidin-2-ylamino)-phenyl]-benzamide(I) where R represents methyl, X represents CH, Y represents zero and n=2

In the first instance, 3,5-Bis trifluoro methyl benzoyl chloride which is used as one of the starting material is prepared as follows:

Thionyl chloride (2.04 kg, 17.2 mol) is added over a period of 15 min to a solution of 3,5-Bis trifluoro methyl benzoic acid (855.0 g, 3.3 mol) and D.M.F. (9 ml) in chloroform (9 L) at room temperature. The reaction mixture is heated to reflux temperature for 1 hour. The excess of thionyl chloride is removed by co-distillation with chloroform under reduced pressure at 40° C. After the end of the distillation, the resulting 3,5-Bis trifluoro methyl benzoyl chloride is cooled down to room temperature and dissolved in 700 ml chloroform.

A solution of N-(5-amino-2-methylphenyl)-(3-pyridyl)-2-pyrimidine amine of the formula (XVII) (0.73 kgs, 2.64 mol) in chloroform (9 L) is cooled to −5° C. and triethyl amine (1.03 kg, 10.2 mol) of is added. 3,5-Bis trifluoro methyl benzoyl chloride in chloroform is added drop wise at −5° C. over a period of 60-75 min. The resulting suspension is stirred for 1 hr at −5° C. The suspension is filtered, washed with D.M. water and methanol vacuum to give 1.3 kg of wet crude title compound which on recrystallization from methanol yielded 0.82 kgs (60%) of (3,5-Bis trifluoromethyl)-N-[4-methyl-3-(4-pyridin-3-yl-pyrimidin-2-ylamino)-phenyl]-benzamide (I) where R represents methyl, X represents CH and n=2 as cream colored crystals (99.9% purity by HPLC) MR-248-250° C.

EXAMPLE-5

Preparation of (2-trifluoromethyl)-N-[4-methyl-3-(4-pyridin-3-yl-pyrimidin-2-ylamino)-phenyl]-benzamide (I) where R represents methyl, X represents CH, Y represents zero and n=1

Step I: Preparation of novel (2-trifluoromethyl)-N-(4-methyl-3-nitro-phenyl)-)-benzamide of the formula (XIII) where R represents methyl, X represents CH, Y represents zero and n=1

In the first instance, trifluoro methyl benzoyl chloride which is used as one of the starting material is prepared as follows:

Thionyl chloride (62.4 g, 0.53 mol) is added over a period of 15 min to a solution of 2-trifluoro methyl benzoic acid (Aldrich) (20.0 g, 0.106 mol) in chloroform (200 ml) at room temperature. The reaction mixture is heated to reflux temperature for 1 hour. The excess of thionyl chloride is removed by co-distillation with chloroform under reduced pressure at 40° C. After the end of the distillation, the resulting trifluoro methyl benzoyl chloride is cooled down to room temperature and dissolved in 100 ml chloroform. A solution of 4-methyl-3-nitroaniline (9.80 g, 0.06 mol) in chloroform (120 ml) is cooled to −5° C. and triethyl amine (32.2 g, 0.32 mol) of is added. Trifluoromethyl benzoyl chloride in chloroform prepared as described above is added drop wise at −5° C. over a period of 30-45 min. The resulting suspension is stirred for 1 hr at −5° C. The suspension is distilled to a residual volume of 150 ml and filtered, washed with chilled chloroform and dried in vacuum to give 19.0 g of novel (2-trifluoromethyl)-N-(4-methyl-3-nitro-phenyl)-benzamide of the formula (XIII) where R represents methyl, X represents CH and n=1 (92%) as pale yellow crystals (97.50% purity by HPLC) MR-120-130° C.

Step II: Preparation of Novel (2-trifluoromethyl N-(3-amino-4-methyl-phenyl))-benzamide of the formula (XIV) where R represents methyl, X represents CH, Y represents zero and n=1

A suspension of (2-trifluoromethyl)-N-(4-methyl-3-nitro-phenyl)-benzamide of the formula (XIII) (19 g, 0.058 moles) prepared by the process described in step I and stannous chloride (59.5 g, 0.26 moles) in absolute ethanol (100 ml) is heated to reflux temperature for 30 min. The resulting suspension is then cooled to room temperature and quenched into 1 L of ice cold water. The reaction mixture $P^H$ is adjusted to 8.0 with 0.5 L of 5% sodium hydroxide solution and extracted with 2×0.5 L of ethyl acetate. The ethyl acetate layer is washed successively with water and brine and dried over sodium sulfate. The ethyl acetate is distilled completely and 100 ml of hexane is added to the residue and filtered. The filtered cake is dried in vacuum at 60° C. to give 14.0 g of novel (2-trifluoromethyl)-N-(3-amino-4-methyl-phenyl)-benzamide of the formula (XIV) where R represents methyl, X represents CH and n=1 (83%) as yellow crystals (98.4% purity by HPLC) MR-128-135° C.

Step III: Preparation of (2-trifluoromethyl)-N-(3-guanidino-4-methyl-phenyl)-benzamide of the formula (XV) where R represents methyl, X represents CH, Y represents zero and n=1

A suspension of (2-trifluoromethyl)-N-(3-amino-4-methyl-phenyl)-benzamide of the formula (XIV) prepared by the process described in step (II) (14 g, 0.047 mol) in n-butanol (100 ml) is treated sequentially with concentrated nitric acid until the pH reaches 2.5 (2.6 g) and with a solution of cyanamide (2.5 g, 0.06 mol) in water (3 ml) over a period of 10 min. The resulting reaction mixture is stirred at reflux temperature for 4-6 hrs. The reaction mixture is then distilled off completely under vacuum and the residue is allowed to cool down to room temperature. A mixture of 50 ml of methanol and 50 ml of IPE is added to the reaction mass and stirred at room temperature for 1 hr. The product is filtered off with suction, washed with a mixture of methanol and IPE (3×20 ml) and dried in vacuum at 60° C. to give 8.6 g of the nitrate salt of (2-trifluoromethyl)-N-(3-guanidino-4-methyl-phenyl)-benzamide of the formula (XV), where R represents methyl, X represents CH and n=1 52% of theory (99.1% purity by HPLC) MR-160-165° C.

Step (IV): Preparation of (2-trifluoromethyl)-N-[4-methyl-3-(4-pyridin-3-yl-pyrimidin-2-ylamino)-phenyl]-benzamide of the formula (I) where R represents methyl, X represents CH, Y represents zero and n=1

A suspension of nitrate salt of N-(3-guanidino-4-methyl-phenyl)-(2-trifluoromethyl)-benzamide nitrate prepared by the process described in step (XV) (8.6 g, 0.02 mol) in n-butanol (60 ml) under an atmosphere of nitrogen is treated successively with sodium hydroxide flakes (1.4 g, 0.03 mol) and 3-dimethylamino-1-pyridin-3-yl-propenone (3.72 g, 0.02 mol). The resulting suspension is heated to reflux temperature for 2 hrs. The reaction mixture becomes a homogeneous deep orange solution and dimethylamine is removed by the distillation of n-butanol. Reaction mass is cooled down to RT and a mixture of water and chloroform (50 ml+50 ml) is added and chloroform layer is separated out. The chloroform layer is washed with water and distilled to a residual volume of 10 ml. Ethyl acetate (40 ml) is added to the reaction mass and filtered off with suction, the isolated solid is washed with ethyl acetate (2×10 ml) and water (2×10 ml) and dried in vacuum at 60° C. Yield: 6.2 g of novel (2-trifluoromethyl)-N-[4-methyl-3-(4-pyridin-3-yl-pyrimidin-2-ylamino)-phenyl]-benzamide of the formula (I) where R represents methyl, X represents CH and n=1 64% based on theory, as off white crystals. MR-206-207° C.

$^1$H-NMR (400 MHz, DMSO-d$_6$, δ):

2.2 (s, 3H); 7.20-9.28 (Aryl, 13H); 10.4 (s, 1H)

| Analysis | $C_{24}H_{18}F_3N_5O$ |
|---|---|
| Molecular weight | 449.0 |
| IR | KBR Disc |
| —NH—C=O | at 3431.2 cm$^{-1}$ |
| —NH—C=O | At 1655.9 cm$^{-1}$ |

EXAMPLE-6

Alternative Process for the Preparation of (2-trifluoromethyl)-N-[4-methyl-3-(4-pyridin-3-yl-pyrimidin-2-ylamino)-phenyl]-benzamide (I) where R represents methyl, X represents CH, Y represents zero and n=1

In the first instance, 2-trifluoro methyl benzoyl chloride which is used as one of the starting material is prepared as follows:

Thionyl chloride (156 g, 1.3 mol) is added over a period of 15 min to a solution of 2-trifluoro methyl benzoic acid (50.0 g, 0.26 mol) in chloroform (250 ml) at room temperature. The reaction mixture is heated to reflux temperature for 1 hour. The excess of thionyl chloride is removed by co-distillation with chloroform under reduced pressure at 40° C. After the end of the distillation, the resulting trifluoro methyl benzoyl chloride is cooled down to room temperature and dissolved in 100 ml chloroform.

A solution of N-(5-amino-2-methylphenyl)-(3-pyridyl)-2-pyrimidine amine of the formula (XVII) (55 g, 0.20) in chloroform (440 ml) is cooled to −5° C. and triethyl amine (79.6 g, 0.788 mol) is added. Trifluoromethyl benzoyl chloride in chloroform prepared as described above is added drop wise at −5° C. over a period of 30-45 min. The resulting suspension is stirred for 1 hr at −5° C. The suspension is filtered, washed with D.M. water and methanol and dried in vacuum to give 51.9 g (58%) of novel 4-(2-trifluoromethyl)-N-[4-methyl-3-(4-pyridin-3-yl-pyrimidin-2-ylamino)-phenyl]-benzamide (I) where R represents methyl, X represents CH and n=1 as pale yellow crystals (99.50% purity by HPLC)

EXAMPLE-7

Preparation of (6-trifluoromethyl)-N-[4-methyl-3-(4-pyridin-3-yl-pyrimidin-2-ylamino)-phenyl]-Nicotinamide (I) where R represents methyl, X represents N, Y represents zero and n=1

Step I: Preparation of novel (6-trifluoromethyl)-N-(4-methyl-3-nitro-phenyl)-)-benzamide of the formula (XIII) where R represents methyl, X represents N, Y represents zero and n=1

In the first instance, 6-trifluoromethyl Nicotinoyl chloride which is used as one of the starting material is prepared as follows.

Thionyl chloride (15.6 g, 0.13 mol) is added over a period of 15 min to a solution of 6-trifluoromethyl Nicotinic acid (GEORGANICS, consortinum, slovak Republic) (5.0 g, 0.026 mol) in chloroform (100 ml) at room temperature. The reaction mixture is heated to reflux temperature for 1 hour. The excess of thionyl chloride is removed by co-distillation with chloroform under reduced pressure at 40° C. After the end of the distillation, the resulting 6-trifluoromethyl Nicotinoyl chloride is cooled down to room temperature and dissolved in 10 ml chloroform. A solution of 4-methyl-3-nitroaniline (2.4 g, 0.016 mol) in chloroform (50 ml) is cooled to −5° C. and triethyl amine (8.0 g, 0.08 mol) of is added. 6-trifluoromethyl Nicotinoyl chloride in chloroform prepared as described above is added drop wise at −5° C. over a period of 30 min. The resulting suspension is stirred for 1 hr at −5° C. The suspension is filtered, washed with chilled chloroform and dried in vacuum to give 3.6 g of novel (6-trifluoromethyl)-N-(4-methyl-3-nitro-phenyl)-Nicotinamide of the formula (XIII) where R represents methyl, X represents N and n=1 (70%) as pale yellow crystals (98.0% purity by HPLC)

MR-167-171° C.

Step II: Preparation of novel (6-trifluoromethyl)-N-(3-amino-4-methyl-phenyl) Nicotinamide—of the formula (XIV) where R represents methyl, X represents N, Y represents zero and n=1

A suspension of (6-trifluoromethyl)-N-(4-methyl-3-nitro-phenyl)-nicotinamide of the formula (XIII) (3.6 g, 0.011 moles) prepared by the process described in step I and stannous chloride (12.4 g, 0.055 moles) in absolute ethanol (25 ml) is heated to reflux temperature for 30 min. The resulting suspension is then cooled to room temperature and quenched into 0.28 L of ice cold water. The reaction mixture $P^H$ is adjusted to 8.0 with of 5% sodium hydroxide solution and extracted with 2×50 ml of ethyl acetate. The ethyl acetate layer is washed successively with water and brine and dried over sodium sulfate. The ethyl acetate is distilled completely and 10 ml of hexane is added to the residue and filtered. The filtered cake is dried in vacuum at 60° C. to give 3.0 g of novel (3-trifluoromethyl)-N-(3-amino-4-methyl-phenyl)-benzamide of the formula (XIV) where R represents methyl, X represents N and n=1 (92%) as yellow crystals. (98% purity by HPLC) MR-174-180.5 Deg C.

Step III: Preparation of (6-trifluoromethyl)-N-(3-guanidino-4-methyl-phenyl)-Nicotinamide of the formula (XV) where R represents methyl, X represents N, Y represents zero and n=1

A suspension of (6-trifluoromethyl)-N-(3-amino-4-methyl-phenyl)-Nicotinamide of the formula (XIV) prepared by the process described in step (II) (3.0 g, 0.01 mol) in n-butanol (20 ml) is treated sequentially with concentrated nitric acid until the pH reaches 2.5 (0.65 g) and with a solution of cyanamide (0.64 g, 0.015 mol) in water (1 ml) over a period of 5 min. The resulting reaction mixture is stirred at reflux temperature for 5 hrs. The reaction mixture is then distilled off completely under vacuum and the residue is allowed to cool down to room temperature. A mixture of 12 ml of methanol and 12 ml of IPE is added to the reaction mass and stirred at room temperature for 1 hr. The product is filtered off with suction, washed with a mixture of methanol and IPE (3×10 ml) and dried in vacuum at 60° C. to give 1.70 g of the nitrate salt of (6-trifluoromethyl)-N-(3-guanidino-4-methyl-phenyl)-Nicotinamide of the formula (XV), where R represents methyl, X represents N and n=1 50% of theory (99.1% purity by HPLC) MR-287.6-292.4° C.

Step (IV): Preparation of (6-trifluoromethyl)-N-[4-methyl-3-(4-pyridin-3-yl-pyrimidin-2-yl amino)-phenyl]-Nicotinamide of the formula (I) where R represents methyl, X represents N, Y represents zero and n=1

A suspension of nitrate salt of (6-trifluoromethyl)-N-(3-guanidino-4-methyl-phenyl)-nicotinamide nitrate prepared by the process described in step (XV) (1.7 g, 0.005 mol) in n-butanol (12 ml) under an atmosphere of nitrogen is treated successively with sodium hydroxide flakes (0.22 g, 0.005 mol) and 3-dimethylamino-1-pyridin-3-yl-propenone (0.85 g, 0.005 mol). The resulting suspension is heated to reflux temperature for 2 hrs. The reaction mixture becomes a homogeneous deep orange solution and dimethylamine is removed by the distillation of n-butanol. Reaction mass is cooled down to RT and a mixture of water and chloroform (50 ml+50 ml) is added and chloroform layer is separated out. The chloroform layer is washed with water and distilled to a residual volume of 5 ml. Ethyl acetate (25 ml) is added to the reaction mass and filtered off with suction, the isolated solid is washed with ethyl acetate and water and dried in vacuum at 60° C. Yield: 1.4 g of novel (6-trifluoromethyl)-N-[4-methyl-3-(4-pyridin-3-yl-pyrimidin-2-yl amino)-phenyl]-Nicotinamide of the formula (I) where R represents methyl, X represents N and n=1 62% based on theory, as pale yellow crystals.
(99.9% purity by HPLC). MR-243-244° C.
$^1$H-NMR (400 MHz, DMSO-d$_6$, δ):
2.2 (s, 3H); 7.20-9.28 (Aryl, 12); 10.7 (s, 1H)

| Analysis | $C_{23}H_{17}F_3N_6O$ |
|---|---|
| Molecular weight | 450.0 |
| IR | KBR Disc |
| —NH—C=O | at 3444 cm$^{-1}$ |
| —NH—C=O | At 1648 cm$^{-1}$ |

EXAMPLE-8

Alternative Process for the Preparation of (6-trifluoromethyl)-N-[4-methyl-3-(4-pyridin-3-yl-pyrimidin-2-ylamino)-phenyl]-Nicotinamide (I) where R represents methyl, X represents N, Y represents zero and n=1

In the first instance, 6-trifluoromethyl Nicotinoyl chloride which is used as one of the starting material is prepared as follows.

Thionyl chloride (15.6 g, 0.13 mol) is added over a period of 15 min to a solution of 6-trifluoromethyl Nicotinic acid (GEORGANICS, consortinum, slovak Republic) (5.0 g, 0.026 mol) in chloroform (100 ml) at room temperature. The reaction mixture is heated to reflux temperature for 1 hour. The excess of thionyl chloride is removed by co-distillation with chloroform under reduced pressure at 40° C. After the end of the distillation, the resulting 6-trifluoromethyl Nicotinoyl chloride is cooled down to room temperature and dissolved in 10 ml chloroform. A solution of N-(5-amino-2-methylphenyl)-4-(3-pyridyl)-2-pyrimidine amine of the formula (XVII) (4.8 g, 0.016 mol) in chloroform (50 ml) is cooled to −5° C. and triethyl amine (8.0 g, 0.08 mol) of is added. 6-trifluoromethyl Nicotinoyl chloride in chloroform prepared as described above is added drop wise at −5° C. over a period of 30 min. The resulting suspension is stirred for 1 hr at −5° C. The suspension is filtered, washed with D.M. water and methanol and dried in vacuum to give 4.3 g of novel (6-trifluoromethyl)-N-[4-methyl-3-(4-pyridin-3-yl-pyrimidin-2-ylamino)-phenyl]-Nicotinamide (I) where R represents methyl, X represents N and n=1 (60%) as cream coloured crystals (98.0% purity by HPLC)
MR-242-244° C.

EXAMPLE-9

Preparation of (5-trifluoromethyl)-N-[4-methyl-3-(4-pyridin-3-yl-pyrimidin-2-ylamino)-phenyl]-Nicotinamide (I) where R represents methyl, X represents N, Y represents zero and n=1

Step I: Preparation of novel (5-trifluoromethyl)-N-(4-methyl-3-nitro-phenyl)-Nicotinamide of the formula (XIII) where R represents methyl, X represents N, Y represents zero and n=1

In the first instance, 5-trifluoromethyl Nicotinoyl chloride which is used as one of the starting material is prepared as follows.

Thionyl chloride (15.6 g, 0.13 mol) is added over a period of 15 min to a solution of 5-trifluoromethyl Nicotinic acid (GEORGANICS, consortinum, slovak Republic) (5.0 g, 0.026 mol) in chloroform (100 ml) at room temperature. The reaction mixture is heated to reflux temperature for 1 hour. The excess of thionyl chloride is removed by co-distillation with chloroform under reduced pressure at 40° C. After the end of the distillation, the resulting 6-trifluoromethyl Nicotinoyl chloride is cooled down to room temperature and dissolved in 10 ml chloroform. A solution of 4-methyl-3-nitroaniline (2.4 g, 0.016 mol) in chloroform (50 ml) is cooled to −5° C. and triethyl amine (8.0 g, 0.08 mol) of is added. 6-trifluoromethyl Nicotinoyl chloride in chloroform prepared as described above is added drop wise at −5° C. over a period of 30 min. The resulting suspension is stirred for 1 hr at −5° C. The suspension is filtered, washed with chilled chloroform and dried in vacuum to give 3.6 g of novel (5-trifluoromethyl)-N-(4-methyl-3-nitro-phenyl)-Nicotinamide of the formula (XIII) where R represents methyl, X represents N and n=1 (70%) as pale yellow crystals
(98.0% purity by HPLC)
MR-167-171° C.

Step II: Preparation of novel (5-trifluoromethyl)-N-(3-amino-4-methyl-phenyl)-Nicotinamide—of the formula (XIV) where R represents methyl, X represents N, Y represents zero and n=1

A suspension of (5-trifluoromethyl)-N-(4-methyl-3-nitro-phenyl)-nicotinamide of the formula (XIII) (3.6 g, 0.011 moles) prepared by the process described in step I and stannous chloride (12.4 g, 0.055 moles) in absolute ethanol (25 ml) is heated to reflux temperature for 30 min. The resulting suspension is then cooled to room temperature and quenched into 0.28 L of ice cold water. The reaction mixture $P^H$ is adjusted to 8.0 with of 5% sodium hydroxide solution and extracted with 2×50 ml of ethyl acetate. The ethyl acetate layer is washed successively with water and brine and dried over sodium sulfate. The ethyl acetate is distilled completely and 10 ml of hexane is added to the residue and filtered. The filtered cake is dried in vacuum at 60° C. to give 3.0 g of novel (5-trifluoromethyl)-N-(3-amino-4-methyl-phenyl)-nicotinamide of the formula (XIV) where R represents methyl, X represents N and n=1 (92%) as yellow crystals. (98% purity by HPLC) MR-174-180.5 Deg C.

Step III: Preparation of (5-trifluoromethyl)-N-(3-guanidino-4-methyl-phenyl)-Nicotinamide of the formula (XV) where R represents methyl, X represents N, Y represents zero and n=1

A suspension of (5-trifluoromethyl)-N-(3-amino-4-methyl-phenyl)-Nicotinamide of the formula (XIV) prepared by the process described in step (II) (3.0 g, 0.01 mol) in n-butanol (20 ml) is treated sequentially with concentrated nitric acid until the pH reaches 2.5 (0.65 g) and with a solution of cyanamide (0.64 g, 0.015 mol) in water (1 ml) over a period of 5 min. The resulting reaction mixture is stirred at reflux temperature for 5 hrs. The reaction mixture is then distilled off completely under vacuum and the residue is allowed to cool down to room temperature. A mixture of 12 ml of methanol and 12 ml of IPE is added to the reaction mass and stirred at room temperature for 1 hr. The product is filtered off with suction, washed with a mixture of methanol and IPE (3×10 ml) and dried in vacuum at 60° C. to give 1.70 g of the nitrate salt of (5-trifluoromethyl)-N-(3-guanidino-4-methyl-phenyl)-Nicotinamide of the formula (XV), where R represents methyl, X represents N and n=1 50% of theory (99.1% purity by HPLC) MR-287.6-292.4° C.

Step (IV): Preparation of (5-trifluoromethyl)-N-[4-methyl-3-(4-pyridin-3-yl-pyrimidin-2-yl amino)-phenyl]-Nicotinamide of the formula (I) where R represents methyl, X represents N, Y represents zero and n=1

A suspension of nitrate salt of (5-trifluoromethyl)-N-(3-guanidino-4-methyl-phenyl)-)-nicotinamide nitrate prepared by the process described in step (XV) (1.7 g, 0.005 mol) in n-butanol (12 ml) under an atmosphere of nitrogen is treated successively with sodium hydroxide flakes (0.22 g, 0.005 mol) and 3-dimethylamino-1-pyridin-3-yl-propenone (0.85 g, 0.005 mol). The resulting suspension is heated to reflux temperature for 2 hrs. The reaction mixture becomes a homogeneous deep orange solution and dimethylamine is removed by the distillation of n-butanol. Reaction mass is cooled down to RT and a mixture of water and chloroform (50 ml+50 ml) is added and chloroform layer is separated out. The chloroform layer is washed with water and distilled to a residual volume of 5 ml. Ethyl acetate (25 ml) is added to the reaction mass and filtered off with suction, the isolated solid is washed with ethyl acetate and water and dried in vacuum at 60° C. Yield: 1.4 g of novel (5-trifluoromethyl)-N-[4-methyl-3-(4-pyridin-3-yl-pyrimidin-2-yl amino)-phenyl]-Nicotinamide of the formula (I) where R represents methyl, X represents N and n=1 62% based on theory, as pale yellow crystals. (99.9% purity by HPLC). MR-243-244° C.
$^1$H-NMR (400 MHz, DMSO-d$_6$, δ):
2.2 (s, 3H); 7.20-9.28 (Aryl, 12); 10.7 (s, 1H)

| Analysis | $C_{23}H_{17}F_3N_6O$ |
| Molecular weight | 450.0 |
| IR | KBR Disc |
| —NH—C=O | at 3444 cm$^{-1}$ |
| —NH—C=O | At 1648 cm$^{-1}$ |

EXAMPLE-10

Alternative process for the Preparation of (5-trifluoromethyl)-N-[4-methyl-3-(4-pyridin-3-yl-pyrimidin-2-ylamino)-phenyl]-Nicotinamide (I) where R represents methyl, X represents N, Y represents zero and n=1

In the first instance, 5-trifluoromethyl Nicotinoyl chloride which is used as one of the starting material is prepared as follows.

Thionyl chloride (15.6 g, 0.13 mol) is added over a period of 15 min to a solution of 5-trifluoromethyl Nicotinic acid (5.0 g, 0.026 mol) in chloroform (100 ml) at room temperature. The reaction mixture is heated to reflux temperature for 1 hour. The excess of thionyl chloride is removed by co-distillation with chloroform under reduced pressure at 40° C. After the end of the distillation, the resulting 6-trifluoromethyl Nicotinoyl chloride is cooled down to room temperature and dissolved in 10 ml chloroform.

A solution of N-(5-amino-2-methylphenyl)-4-(3-pyridyl)-2-pyrimidine amine of the formula (XVII) (4.8 g, 0.016 mol) in chloroform (50 ml) is cooled to −5° C. and triethyl amine (8.0 g, 0.08 mol) of is added. 6-trifluoromethyl Nicotinoyl chloride in chloroform prepared as described above is added drop wise at −5° C. over a period of 30 min. The resulting suspension is stirred for 1 hr at −5° C. The suspension is filtered, washed with D.M. water and methanol and dried in vacuum to give 4.3 g of novel (5-trifluoromethyl)-N-[4-methyl-3-(4-pyridin-3-yl-pyrimidin-2-ylamino)-phenyl]-Nicotinamide (I) where R represents methyl, X represents N and n=1 (60%) as cream coloured crystals (98.0% purity by HPLC)
MR-242-244° C.

EXAMPLE-11

Preparation of (3-trifluoromethylthio)-N-[4-methyl-3-(4-pyridin-3-yl-pyrimidin-2-ylamino)-phenyl]-benzamide of the formula (I) where R represents methyl, X represents CH, Y represents thio and n=1:

Step I: Preparation of novel (3-trifluoromethylthio)-N-(4-methyl-3-nitro-phenyl)-benzamide of the formula (XIII) where R represents methyl, X represents CH, Y represents thio and n=1

In the first instance, (3-trifluoro methylthio) benzoyl chloride which is used as one of the starting material is prepared as follows:
Thionyl chloride (40.0 g, 0.33 mol) is added over a period of 15 min to a solution of (3-trifluoromethylthio)benzoic acid (15.0 g, 0.0675 mol) in chloroform (150 ml) at room temperature. The reaction mixture is heated to reflux temperature for 1 hour. The excess of thionyl chloride is removed by co-distillation with chloroform under reduced pressure at 40° C. After the end of the distillation, the resulting (3-trifluoromethylthio) benzoyl chloride is cooled down to room temperature and dissolved in 15 ml chloroform.

A solution of 4-methyl-3-nitroaniline (6.8 g, 0.045 mol) in chloroform (80 ml) is cooled to −5° C. and triethyl amine (22.77 g, 0.23 mol) of is added. (3-Trifluoromethylthio) benzoyl chloride in chloroform prepared as described above is added drop wise at −5° C. over a period of 15-20 min. The resulting suspension is stirred for 1 hr at −5° C. The suspension is distilled to a residual volume of 20 ml and filtered, washed with chilled chloroform and dried in vacuum to give 12.0 g of novel (3-trifluoromethyl)-N-(4-methyl-3-nitro-phenyl)-benzamide of the formula (IV) where R represents methyl, X represents CH, Y represents thio and n=1 (75%) as pale yellow crystals (98.0% purity by HPLC)

Step II: Preparation of Novel (3-trifluoromethylthio)-N-(3-amino-4-methyl-phenyl)-benzamide of the formula (XIV) where R represents methyl, X represents CH, Y represents thio and n=1

A suspension of (3-trifluoromethylthio)-N-(4-methyl-3-nitro-phenyl)-benzamide of the formula (IV) (10 g, 0.028 moles) prepared by the process described in step I and stannous chloride (31.7 g, 0.14 moles) in absolute ethanol (70 ml) is heated to reflux temperature for 30 min. The resulting suspension is then cooled to room temperature and quenched into 4 L of ice cold water. The reaction mixture $P^H$ is adjusted to 8.0 with 5% sodium hydroxide solution and extracted with 2×250 ml. of ethyl acetate. The ethyl acetate layer is washed successively with water and brine and dried over sodium sulfate. The ethyl acetate is distilled completely and 500 ml of hexane is added to the residue and filtered. The filtered cake is dried in vacuum at 60° C. to give 7.2 g of novel (3-trifluoromethylthio)-N-(3-amino-4-methyl-phenyl)-benzamide of the formula (XIV) where R represents methyl, X represents CH, Y represents thio and n=1 (76%) as yellow crystals Step III: Preparation of—(3-trifluoromethylthio)-N-(3-guanidino-4-methyl-phenyl))-benzamide of the formula (XV) where R represents methyl, X represents CH, Y represents thio and n=1

A suspension of (3-trifluoromethylthio)-N-(3-amino-4-methyl-phenyl)-benzamide of the formula (XIV) prepared by the process described in step (II) (7 g, 0.021 mol) in n-butanol (50 ml) is treated sequentially with concentrated nitric acid until the pH reaches 2.5 (1.3 g) and with a solution of cyanamide (1.3 g, 0.032 mol) in water (1.3 ml) over a period of 10 min. The resulting reaction mixture is stirred at reflux temperature for 6 hrs. The reaction mixture is then distilled off completely under vacuum and the residue is allowed to cool down to room temperature. A mixture of 10 ml of methanol and 10 ml of IPE is added to the reaction mass and stirred at room temperature for 1 hr. The product is filtered off with suction, washed with IPE and dried in vacuum at 60° C. to give 3.9 g of the nitrate salt of (3-trifluoromethylthio)-N-(3-guanidino-4-methyl-phenyl))-benzamide of the formula (XV), where R represents methyl, X represents CH, Y represents thio and n=1 50% of theory (99% area by HPLC)

Step (IV): Preparation of (3-trifluoromethylthio)-N-[4-methyl-3-(4-pyridin-3-yl-pyrimidin-2-ylamino)-phenyl]-benzamide of the formula (I) where R represents methyl, X represents CH, Y represents thio and n=1

A suspension of nitrate salt of (3-trifluoromethylthio)-N-(3-guanidino-4-methyl-phenyl)-benzamide nitrate prepared by the process described in step (iv) (3.5 g, 0.0.0095 mol) in n-butanol (20 ml) under an atmosphere of nitrogen is treated successively with sodium hydroxide flakes (0.38 g, 0.0095 mol) and 3-dimethylamino-1-pyridin-3-yl-propenone (1.66 g, 0.0095 mol). The resulting suspension is heated to reflux temperature for 2 hrs. The reaction mixture becomes a homogeneous deep orange solution and dimethylamine is removed by the distillation of n-butanol. Reaction mass is cooled down to RT and a mixture of water and chloroform is added The chloroform layer is separated out and distilled to yield: 2.7 g of novel (3-trifluoromethylthio)-N-[4-methyl-3-(4-pyridin-3-yl-pyrimidin-2-ylamino)-phenyl]-benzamide of the formula (I) where R represents methyl, X represents CH Y represents thio and n=1 60% based on theory, as pale yellow crystals. (99.7% purity by HPLC).

MR-224.5-226.5° C.

$IC_{50}$-8 nms (FIG. 1), N $^1$H-NMR (400 MHz, DMSO-$d_6$, δ): 2.23 (s, 3H); 7.20-9.28 (Aryl, 13H); 10.42 (s, 1H)

| Analysis | $C_{24}H_{18}F_3N_5O$ |
|---|---|
| Molecular weight | 449.0 |
| IR | KBR Disc |
| —NH—C=O | at 3445 cm$^{-1}$ |
| —NH—C=O | At 1648 cm$^{-1}$ |

EXAMPLE-12

Alternative Preparation of (3-trifluoromethylthio)-N-[4-methyl-3-(4-pyridin-3-yl-pyrimidin-2-ylamino)-phenyl]-benzamide of the formula (I) where R represents methyl, X represents CH, Y represents thio and n=1

In the first instance, (3-trifluoromethylthio) benzoyl chloride which is used as one of the starting material is prepared as follows.

Thionyl chloride (8.0 g, 0.067 mol) is added over a period of 15 min to a solution of 3-(trifluoromethylthio) benzoic acid (3.0 g, 0.0135 mol) in chloroform (50 ml) at room temperature. The reaction mixture is heated to reflux temperature for 1 hour. The excess of thionyl chloride is removed by co-distillation with chloroform under reduced pressure at 40° C. After the end of the distillation, the resulting (3-trifluoromethylthio) benzoyl chloride is cooled down to room temperature and dissolved in 5 ml chloroform.

A solution of N-(5-amino-2-methylphenyl)-4-(3-pyridyl)-2-pyrimidine amine of the formula (XVII) (3.1 g, 0.011 mol) in chloroform (25 ml) is cooled to −5° C. and triethyl amine (4.0 g, 0.04 mol) of is added. 3-trifluoromethylthio benzoyl chloride in chloroform prepared as described above is added drop wise at −5° C. over a period of 30 min. The resulting suspension is stirred for 1 hr at −5° C. The suspension is filtered, washed with chloroform and dried in vacuum to give 3.5 g of novel (3-trifluoromethylthio)-N-[4-methyl-3-(4-pyridin-3-yl-pyrimidin-2-ylamino)-phenyl]-benzamide (I) where R represents methyl, X represents CH, Y represents thio and n=1 (53%) as cream coloured crystals (99.8% purity by HPLC)

MR-224-227° C.

EXAMPLE-13

Preparation of (3-trifluoromethylsulfonyl)-N-[4-methyl-3-(4-pyridin-3-yl-pyrimidin-2-ylamino)-phenyl]-benzamide of the formula (I) where R represents methyl, X represents CH, Y represents sulfonyl and n=1

Step I: Preparation of novel (3-trifluoromethylsulfonyl)-N-(4-methyl-3-nitro-phenyl)-benzamide of the formula (XIII) where R represents methyl, X represents CH, Y represents sulfonyl and n=1

In the first instance, (3-trifluoromethylsulfonyl) benzoyl chloride which is used as one of the starting material is prepared as follows.

Thionyl chloride (8.1 g, 0.068 mol) is added over a period of 15 min to a solution of 3-(trifluoromethylsulfonyl) benzoic acid (3.5 g, 0.0137 mol) in chloroform (50 ml) at room temperature. The reaction mixture is heated to reflux temperature for 1 hour. The excess of thionyl chloride is removed by co-distillation with chloroform under reduced pressure at 40° C. After the end of the distillation, the resulting (3-trifluoromethylsulfonyl) benzoyl chloride is cooled down to room temperature and dissolved in 5 ml chloroform.

A solution of N-(5-amino-2-methylphenyl)-4-(3-pyridyl)-2-pyrimidine amine of the formula (XVII) (3.1 g, 0.011 mol) in chloroform (25 ml) is cooled to −5° C. and triethyl amine (4.0 g, 0.04 mol) of is added. 3-trifluoromethylsulfonyl benzoyl chloride in chloroform prepared as described above is added drop wise at −5° C. over a period of 30 min. The resulting suspension is stirred for 1 hr at −5° C. The suspension is filtered, washed with chloroform and dried in vacuum to give 3.5 g (61% of theory) of novel (3-trifluoromethylthio)-N-[4-methyl-3-(4-pyridin-3-yl-pyrimidin-2-ylamino)-phenyl]-benzamide (I) where R represents methyl, X represents CH, Y represents sulfonyl and n=1 as light yellow colored crystals (99.4% purity by HPLC)
MR-215-218° C.

EXAMPLE-14

Capsules containing 25 mg and 50 mg of the compounds prepared by the process described in the Example-1(3-trifluoromethyl)-N-[4-methyl-3-(4-pyridin-3-yl-pyrimidin-2-ylamino)-phenyl]-benzamide and Example-3(3,5-Bis trifluoromethyl)-N-[4-methyl-3-(4-pyridin-3-yl-pyrimidin-2-ylamino)-phenyl]-benzamide having the following composition are prepared in customary manner

| Ingredient | Compound of formula-I (3,5-Bis trifluoromethyl)-N-[4-methyl-3-(4-pyridin-3-yl-pyrimidin-2-ylamino)-phenyl]-benzamide mg/capsule* | Compound of formula-I (3-trifluoromethyl)-N-[4-methyl-3-(4-pyridin-3-yl-pyrimidin-2-ylamino)-phenyl]-benzamide mg/capsule* |
|---|---|---|
|  | 25.0 | 50.0 |
| PVP | 25.0 | 50.0 |
| Lactose | 127.0 | 77.0 |
| Talc | 0.5 | 0.5 |
| Crospovidone | 20.0 | 20.0 |
| Magnesium stearate | 0.5 | 0.5 |
| SLS | 2.0 | 2.0 |

In Vitro Studies:

Compounds of the formula-I prepared by the process described in (Example-1 and Example-3) are dissolved in cell culture medium DMSO at a concentration of 10 mM for in vitro studies. The stock solution is further diluted with the same cell culture medium and used in concentrations of 0.1-10 μm for the experiments.

Figure 2:
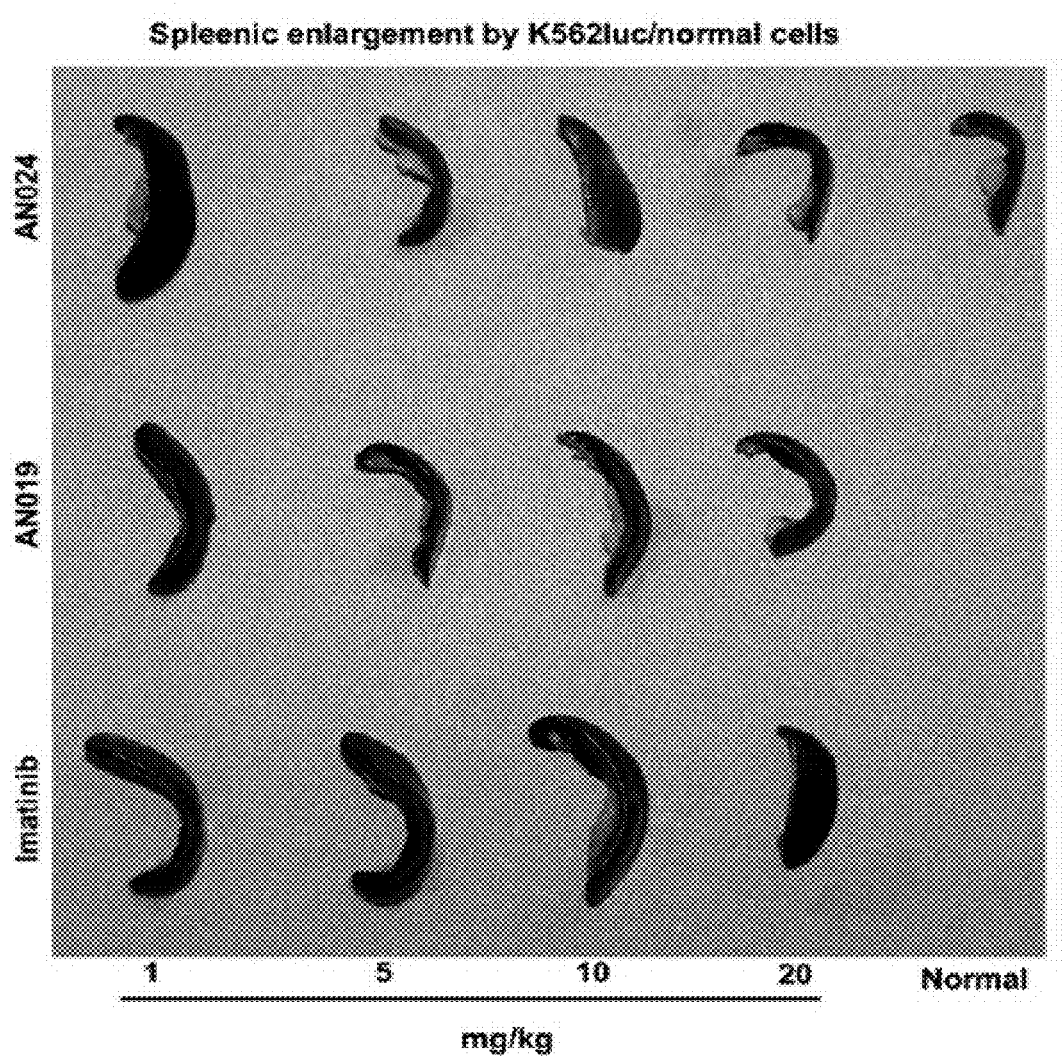
FIG. 2—D32p210 cells were grown in RPMI medium supplemented with 10% FBS in humidified air at 5% $CO_2$ and 37° C. For MTT assay, 5×10³ cells/well were seeded in a 96-well plate and required drug (AN019) concentration ranging from 100 pM to 10 □M was added incubated fro 24 hrs. Cell proliferation was assessed by incubating the cells with 20 □l of MTT (5 mg/ml stock) for additional 3 hrs followed by addition of lysis buffer to dissolve the formazan crystals. After overnight incubation, the absorbance was recorded using ELISA reader at a dual wavelength of 570-630 nm. After a serious of such experiments, a narrower range of concentrations (500 pM to 1 nM) was selected and MTT assay was repeated to determiner the $IC_{50}$ value.
Figure 3A:
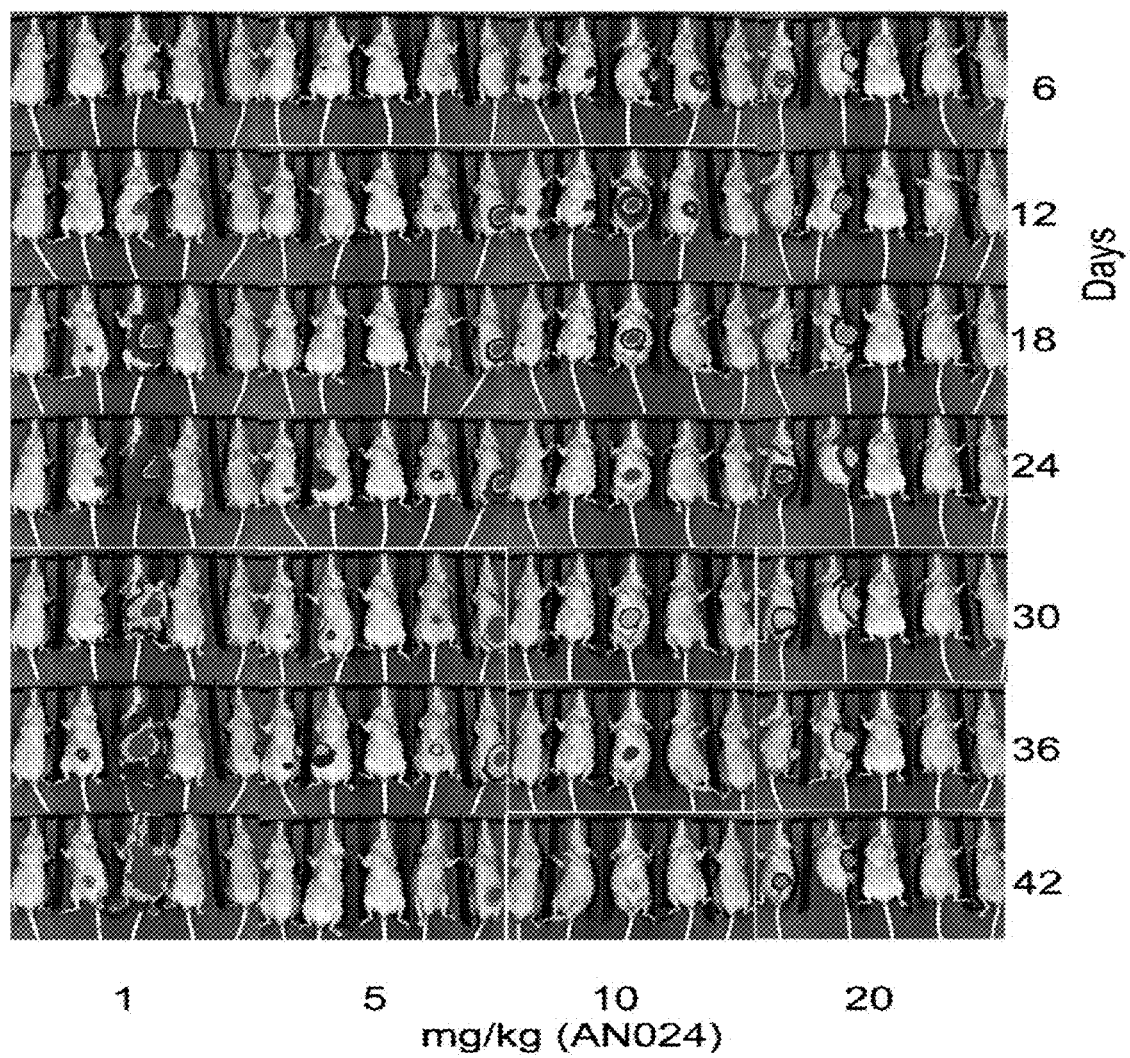
FIG. 3—After treatment cells were lysed and total cellular DNA was extracted and electrophoresed on 1% agarose gel containing 0.05 mg/ml ethidium bromide at 5 V/cm. The gels were then photographed under UV illumination. Lane 1: Control cells; 1 and 2: Cells treated with 10 nM, AN-015; lane 3: Cells treated with 700 pM, AN-019.
Figure 3B:
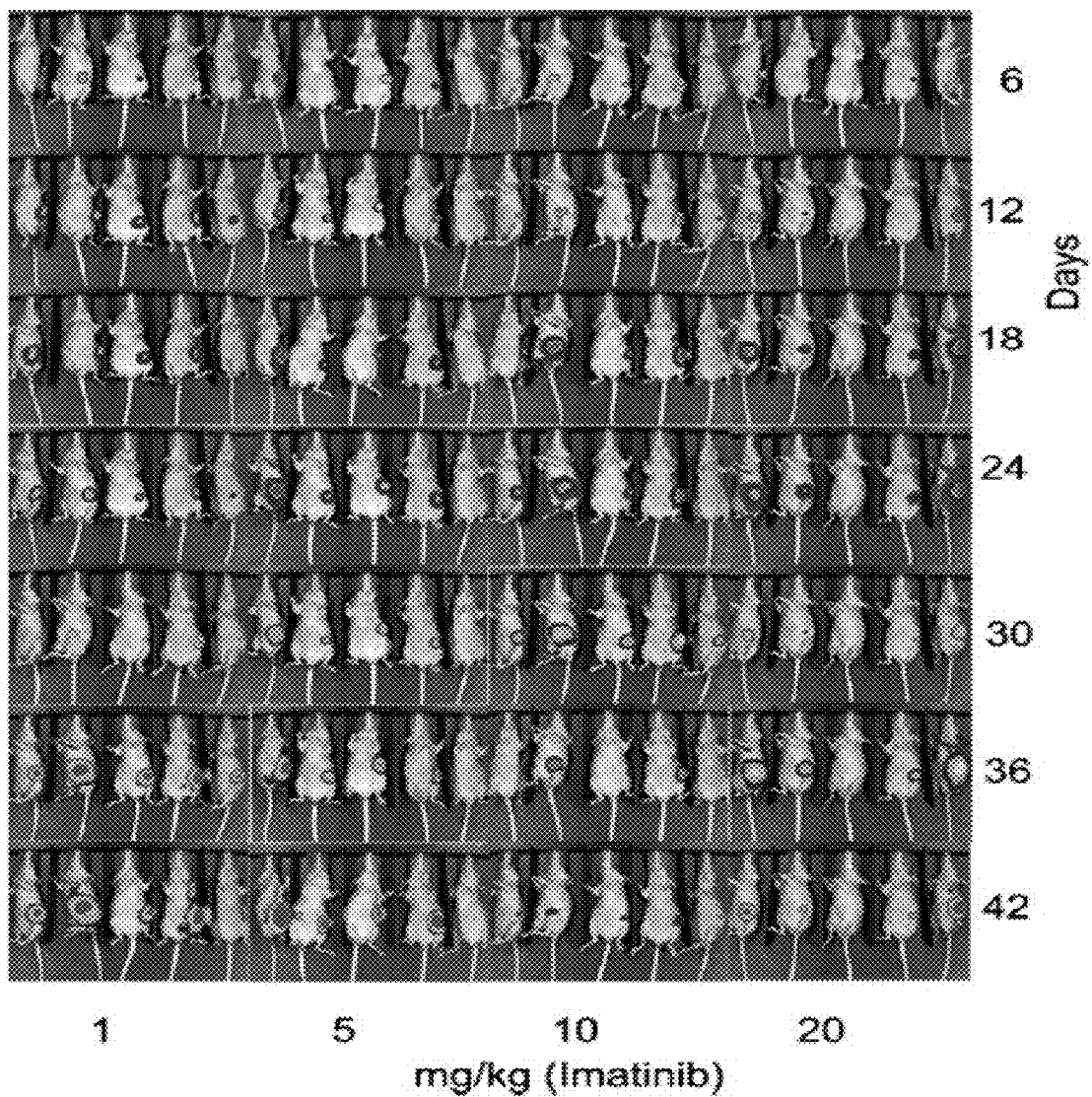

For the study the results of which are disclosed here the BCR-abl positive cell line K562 (the continuous cell line established by Lozzio and Lozzio (1975) from the pleural effusion of a 53 year old female with Chronic Myeloid Leukemia in terminal blast crisis) and D32p210 cell line (a BCR-abl transfected cell line) were used. The K562 and D32p210 cells were grown in RPMI medium supplemented with 10% fetal calf serum at 37° C. and 5% $CO_2$ and 95% air. The cells were sub-cultured for every 24 hours. Cell proliferation by MTT assay was done as follows $5 \times 10^3$ cells were seeded per well in 96-well plate and different concentrations of the compounds of formula (I) ranging from 1 nM to 100 μM were added in quadruplets. After incubating the cells with the compounds for the required time period (24 hrs), 20 μl of 5 mg/ml MTT was added (final concentration 100 μg/ml) and incubated for additional 3 hrs at 37° C. and 5% $CO_2$. After 3 hrs, formazan crystals were dissolved in lysis buffer (10% SDS, 5% Isobutanol, 12 mmol/L HCl) over night at 37° C. Absorbance was measured on ELISA reader at dual wavelength of 570-630 nm. By MTT assay the $IC_{50}$ values of the compounds of formula (I) are computed. The observed values are 8 nms and 0.7 nms respectively as shown in FIG. 1 & FIG. 2 of the drawings accompanying this specification DNA fragmentation assay was done as follows. Cells were treated with compounds of the formula (I) for 24 hrs and the fragmented DNA was isolated using SDS/Proteinase K/Rnase An extraction method, which allows the isolation of only fragmented DNA without contaminating genomic DNA (Nucleic acids Res—22: 5506-5507, 1994). The cells were washed in cold Phosphate Buffered Saline (PBS) and lysed in a buffer containing 50 mM Tris HCl (pH 8.0), 1 mM EDTA, 0.2% triton X-100 for 20 min at 4° C. After centrifugation at 14,000 g for 15 minutes, the supernatant was treated with proteinase K (0.5 mg/ml) and 1% Sodium Dodecyl sulphate (SDS) for 1 hour at 50° C. DNA was extracted twice with buffered phenol and precipitated with 140 mM NaCl and 2 volumes of ethanol at −20° C. overnight. DNA precipitates were washed twice in 70% ethanol, dissolved in Tris-EDTA (TE) and treated for 1 hr at 37° C. with Rnase. Protein microlitres (μl) of DNA was mixed with 3 μl of DNA sample buffer 0.25% bromophenol blue, 0.25% xylene cyanol and 30% glycerol) and was resolved in 1% agarose gel in TBE (44.6 mM Tris, 445 mM, boric acid and 1 mM EDTA) DNA fragmentation was visualized upon staining gel with ethidium bromide (0.5 mg/ml) and exposed to UV light. The presence of apoptosis was indicated by the appearance of ladder of oligonucleosomal DNA fragments that are approximately 180-200 bp multiples. The DNA fragments in the gel clearly indicated that compounds of the formula (I) as specified above induce apoptosis in Bcr-Abl positive cell line K562 as shown in FIG. 3.

Figure 4A:
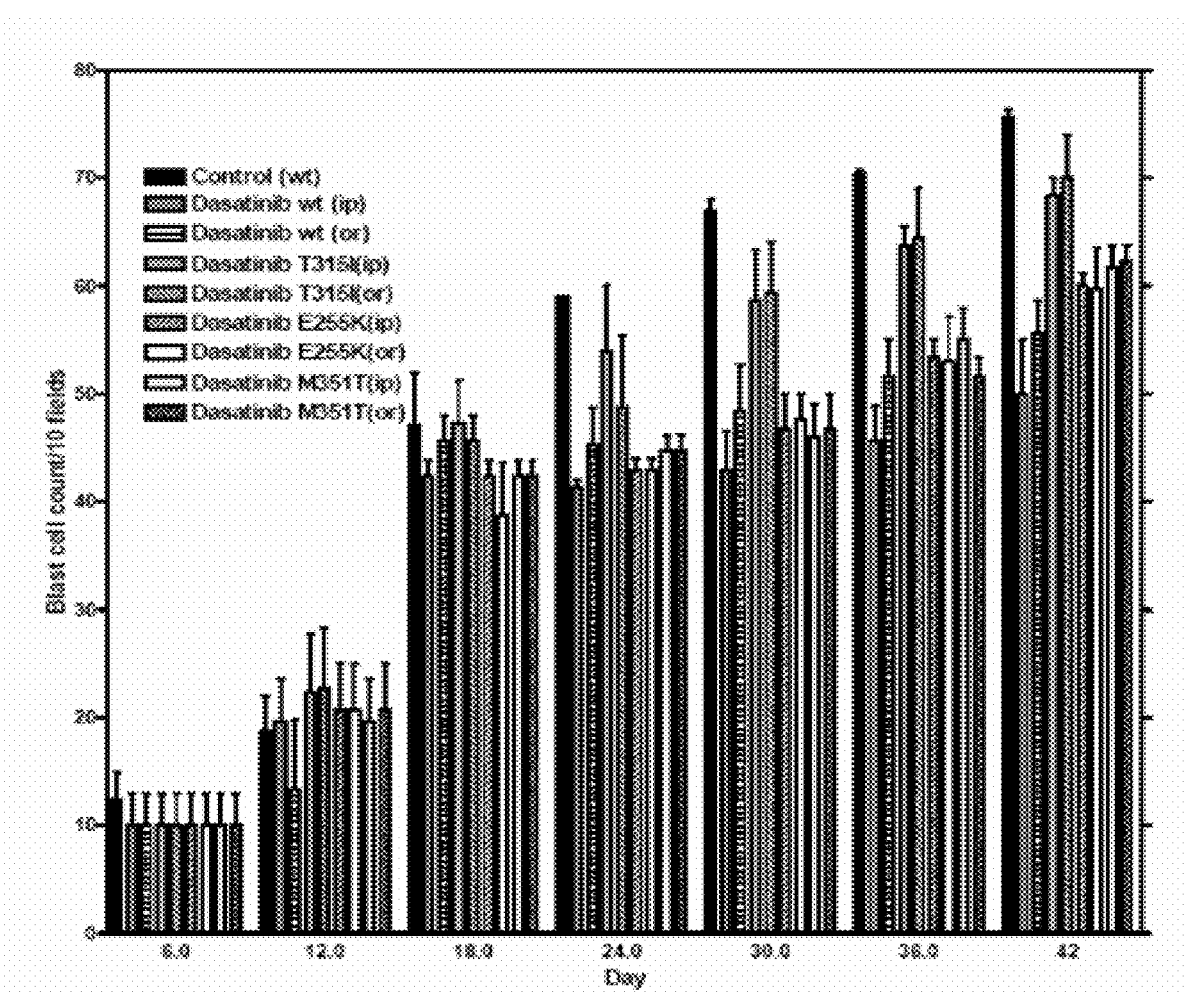
FIG. 4—Cells exposed to 10 nM of AN-015 and 700 pM of AN-019 for 24 h were fixed, and stained with propidium iodide and the DNA content was quantified by FACS. The number of bypodiploid (sub-G0/G1 phase) cells is expressed as a percentage of the total number of cells. (A) Control cells, (B) AN-015, 10 nM, and (C) AN-019, 700 pM.
Figure 4B:
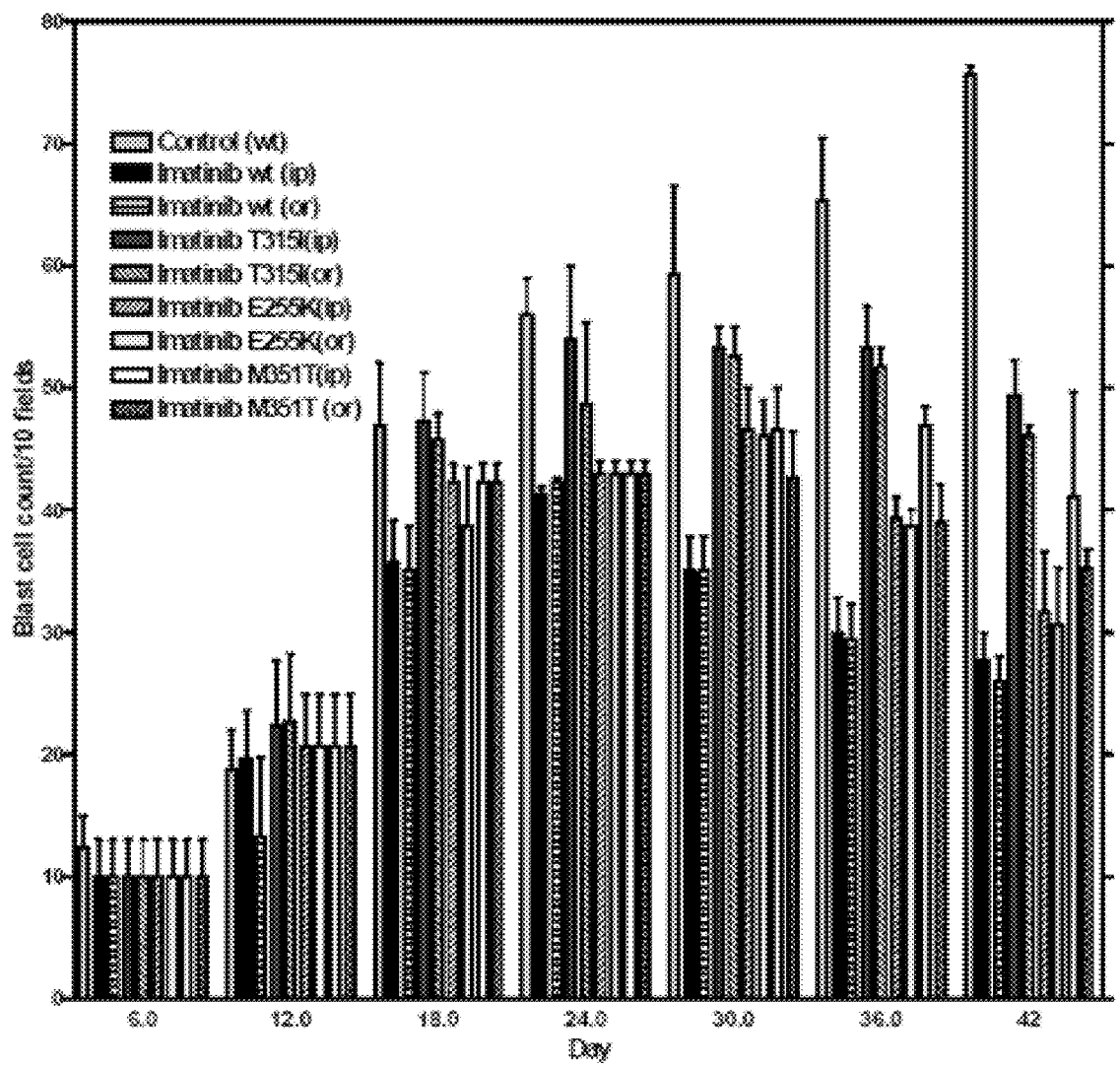
Figure 4C:
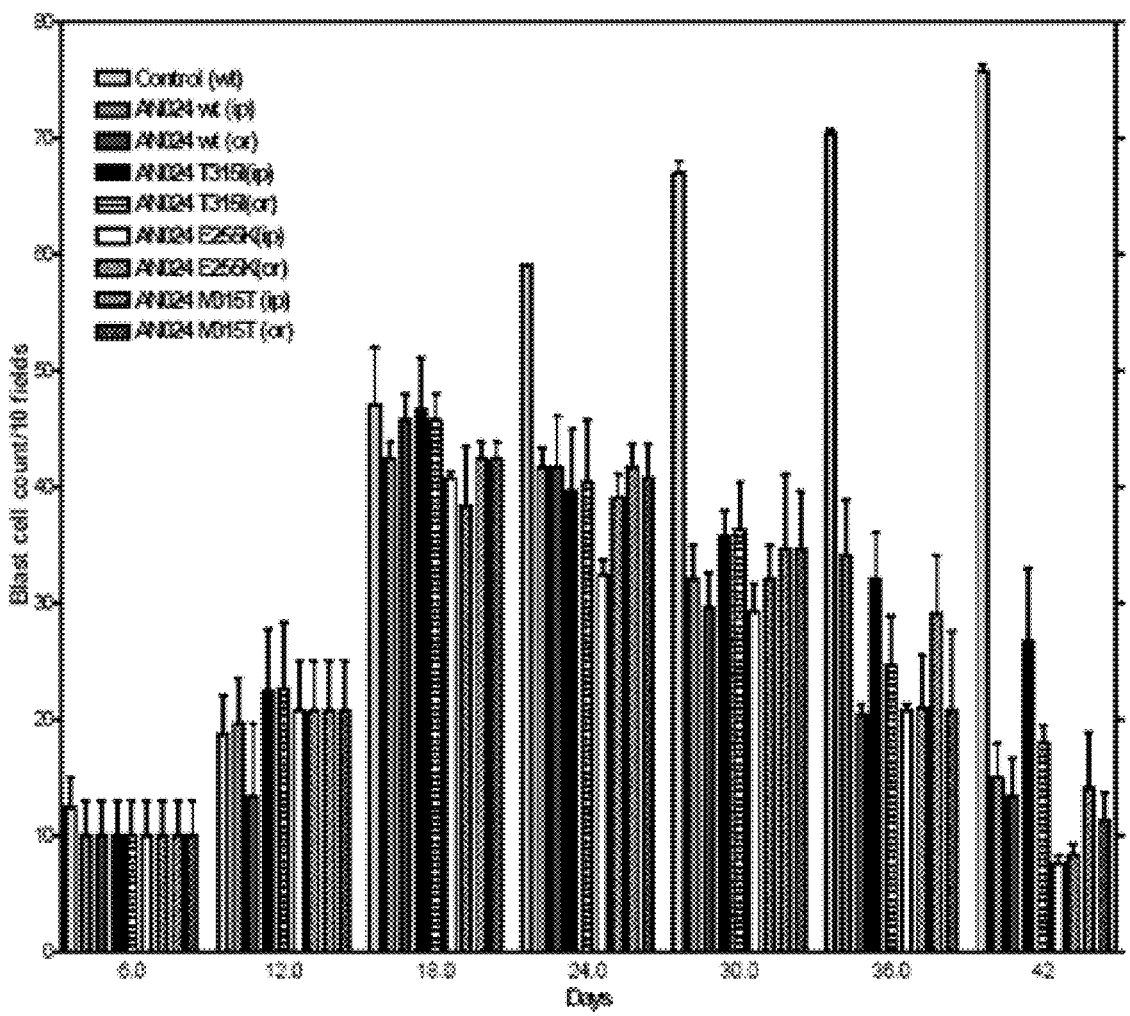
Figure 5A:
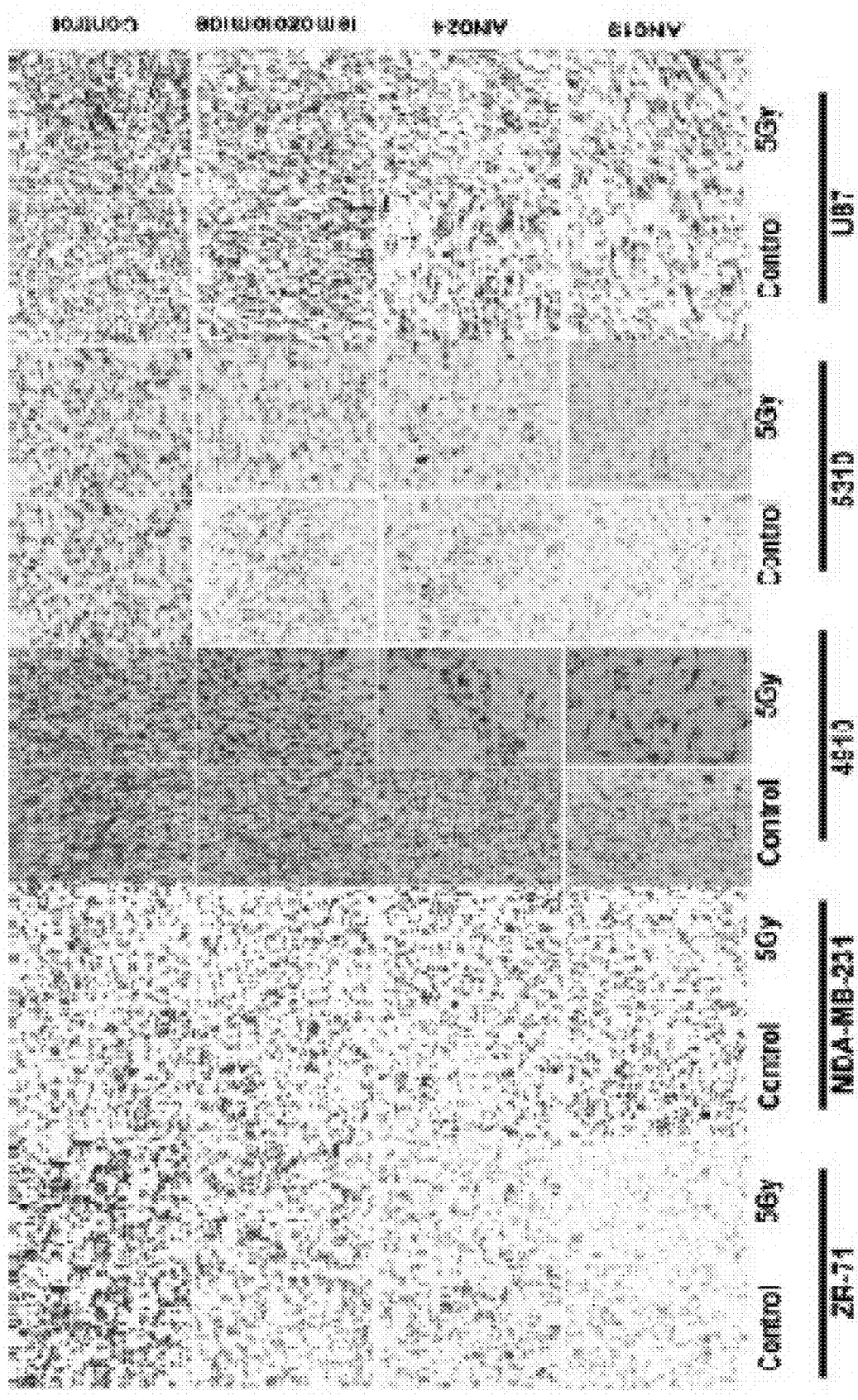
FIG. 5—Cells were photographed under phase contrast microscopy (Magnification 400×). Arrows indicate a typical apoptotic cell with apoptotic bodies. (A) Control cells, (B) AN-015, 10 nM, and (C) AN-019, 700 pM.
Figure 5B:
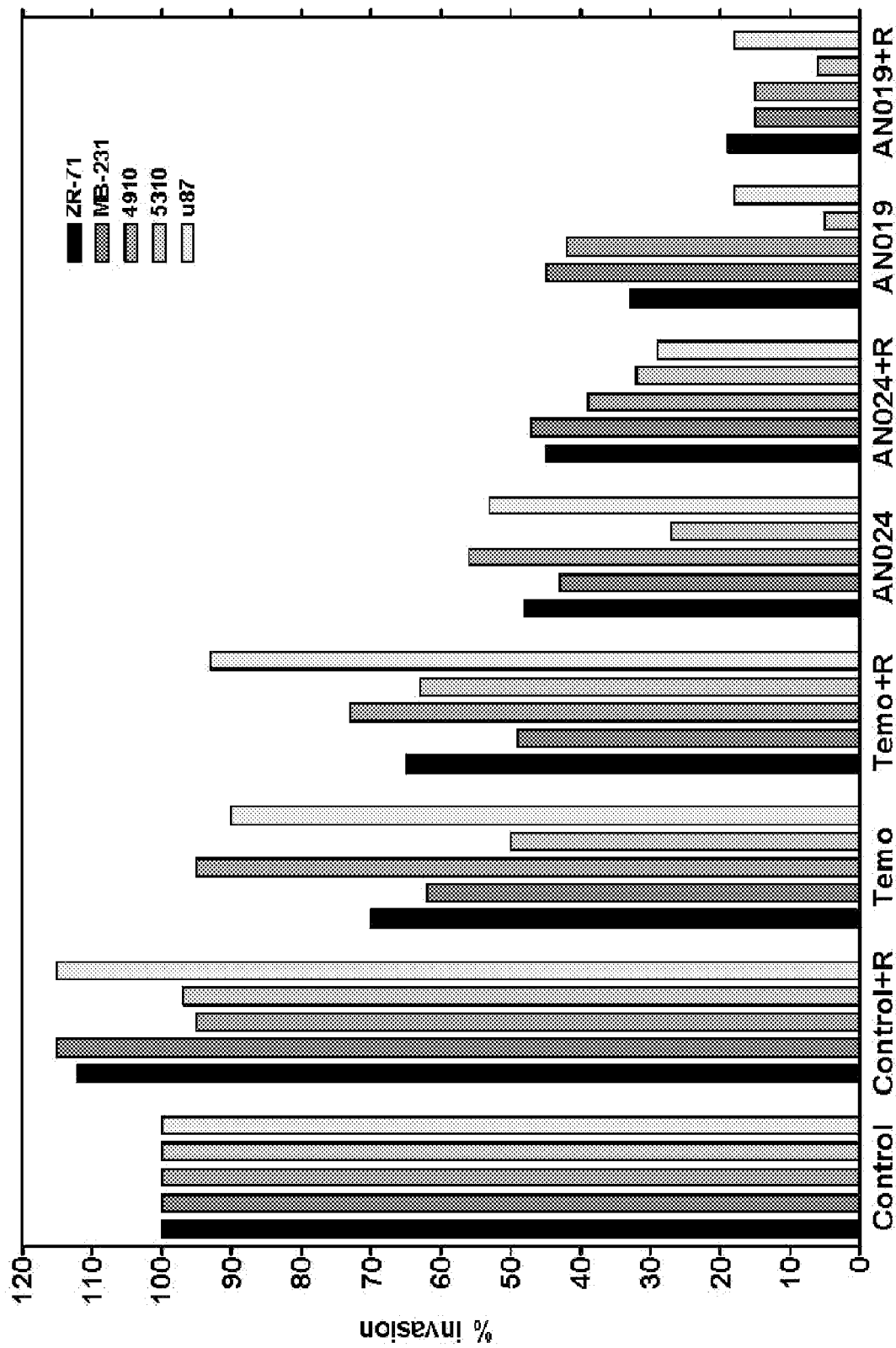
Figure 5C:
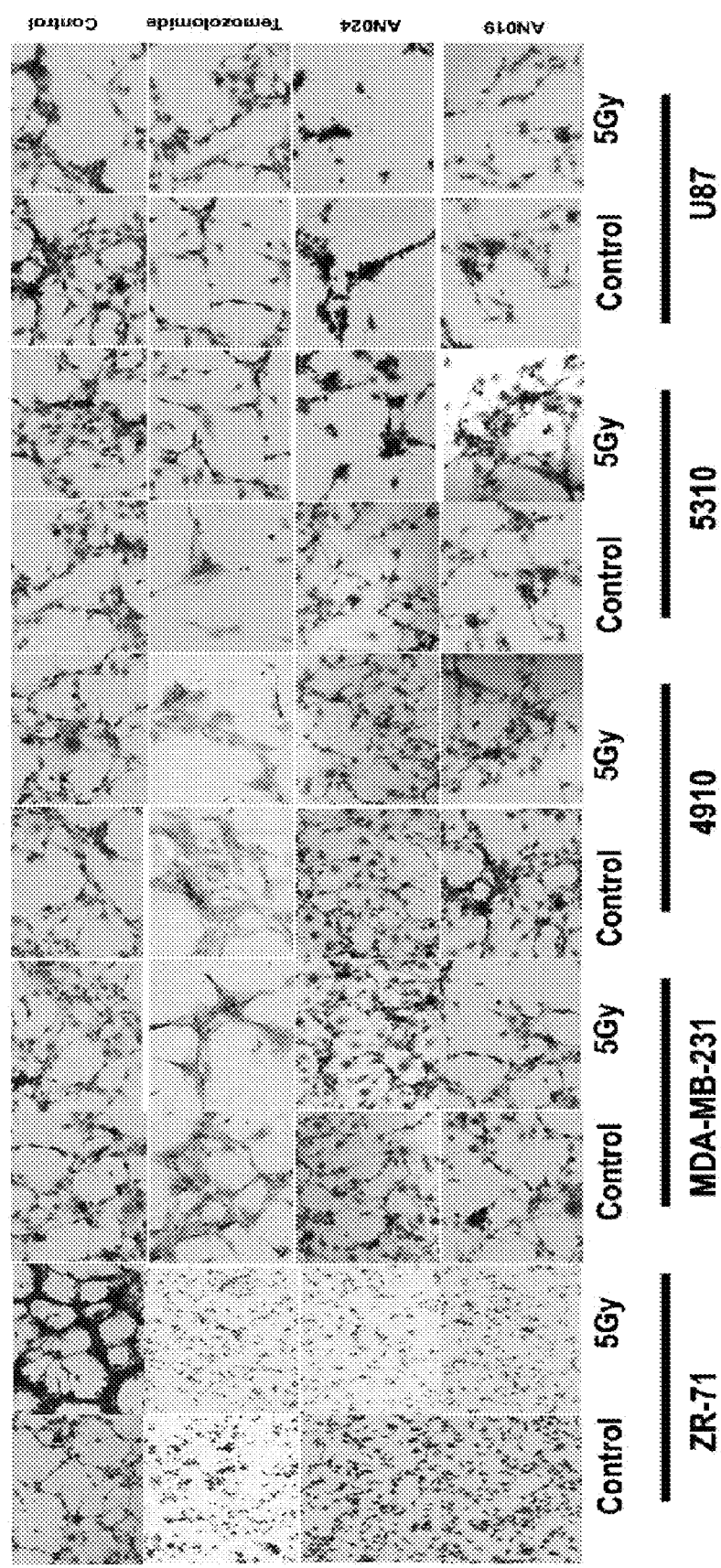
Figure 5D:
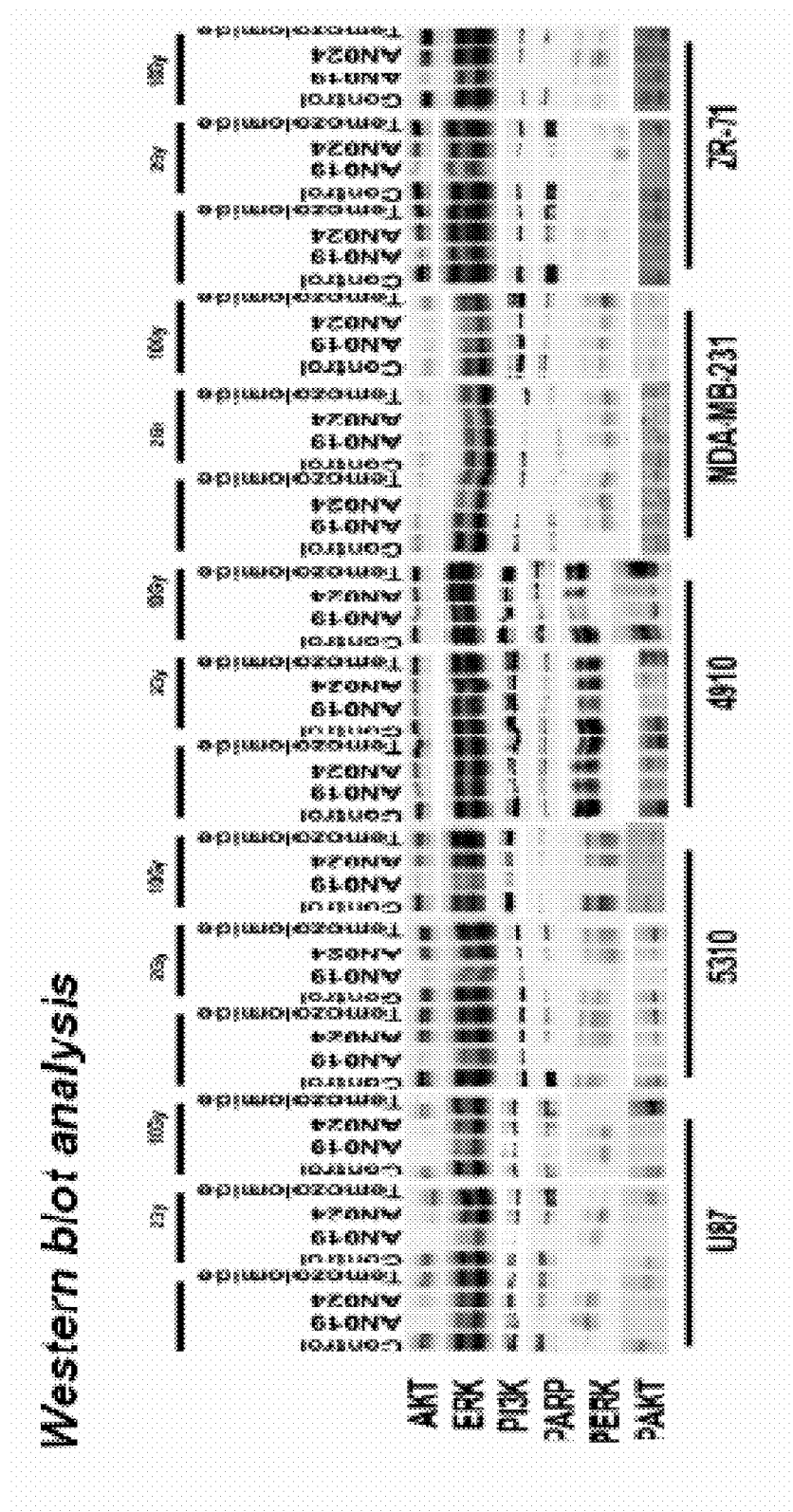

FACS Analysis:

The Fluorescence Activated Cell Sorter (FACS) analysis was done as follows:

To quantitate apoptosis in D32p210 cells, treated with compounds of formula (I) prepared by the process described in (Example-1-Example-3) a flow cytometric analysis using Propidium Iodide (PI) was performed. D32p210 cells were treated with compounds of formula (I) for 24 hrs. After treatment, the cells were washed twice with ice cold PBS and were fixed with 1 ml of ice-cold 70% ethanol gradually and maintained at 4° C. overnight. The cells were harvested by centrifugation at 500×g for 10 min, washed with PBS twice and re-suspended in 1 ml of DNA staining solution containing 0.1% triton X-100, 0.1 mM EDTA, RNase A (50 µg/ml) and 50 µg/ml Propidium Iodide (PI) and incubated for 1 hr in dark at room temperature. The red fluorescence of individual cells was measured with a fluorescence activated cell sorter (FACS) calibur flow cytometer (Becton Dickinson, san Jose, Calif., USA). Minimums of 10,000 events were collected per sample. The relative DNA count per cell was obtained by measuring the fluorescence of PI that bound stoichiometrically to DNA as shown in FIG. 4.

Inhibition constants $K_i$ (binding constant of the inhibitor to enzyme) or $IC_{50}$ (Inhibiting concentration at which growth or activity is inhibition by 50%) values derived from the above mentioned in vitro assays and studies provide a measure of the inhibition capacity of the compounds of formula (I) as specified above is shown in FIG. 5

The In Vitro Kinase Assay was Done as Follows:

The inhibition of the kinase activity of the bcr-abl tyrosine kinase by the compounds of the formula-I (Example-1) was quantified by western blot and densitometric analysis. Briefly, $5 \times 10^6$ 32Dp210 cells were treated with different concentrations of compounds of the formula-I (Example-1, Stage-IV) for 30 min. At the end of the incubation, cells were pelleted, washed with PBS and lysed in 50 µl of lysis buffer containing 10 mM Tris-HCl (pH 8.0), 150 mM NaCl, 1% Triton X-100, 1% Na-deoxycholate, 0.1 mM Na-orthovandate, 50 mM β-glycerophosphate, 50 mM NAF, 1 mM PMSF, 10 µg/ml leupeptin and 10 µg/ml pepstatin. Control was cells without the drug. Equal amount of proteins were resolved on 6% SDS gel and transferred onto nitrocellulose membrane. After blocking with 5% nonfat milk powder, primary antibody (anti-phosphotyrosine antibody) was added. Blot was developed using secondary antibody conjugated to alkaline phosphatase. The band intensity of the bcr-abl kinase was quantified by Densitometric analysis.

The apoptosis induced by compounds of the formula-I (Example-1, Stage-IV) was observed through the phase contrast microscopy. The percentage of apoptosis was 53.3%. compounds of the formula-I prepared by the process described in Example-1 inhibited kinase activity of bcr-abl kinase in 32Dp210 cells in a dose dependent manner and the $IC_{50}$ value was 4 nM as calculated by densitometric analysis.

The Ex-Vivo Study was Done as Follows:

Lymphocytes were extracted from the peripheral blood collected from CML patients and normal persons using Ficoll Histopaque. Briefly, the blood was diluted with 1:1 ratio with 0.96% NaCl(saline) and was overlaid on Ficoll histopaque gradient carefully. The buffy coat of lymphocytes was extracted by centrifugation at 1000 rpm for 20 min at room temperature. The lymphocytes were carefully taken out from the interface using Pasteur pipette and were washed once with RPMI medium.

The lymphocytes isolated as above were cultured in RPMI medium containing 10% FBS at 37° C. and 5% $CO_2$. The cells were subcultured for every 48 hours.

Figure 6A:
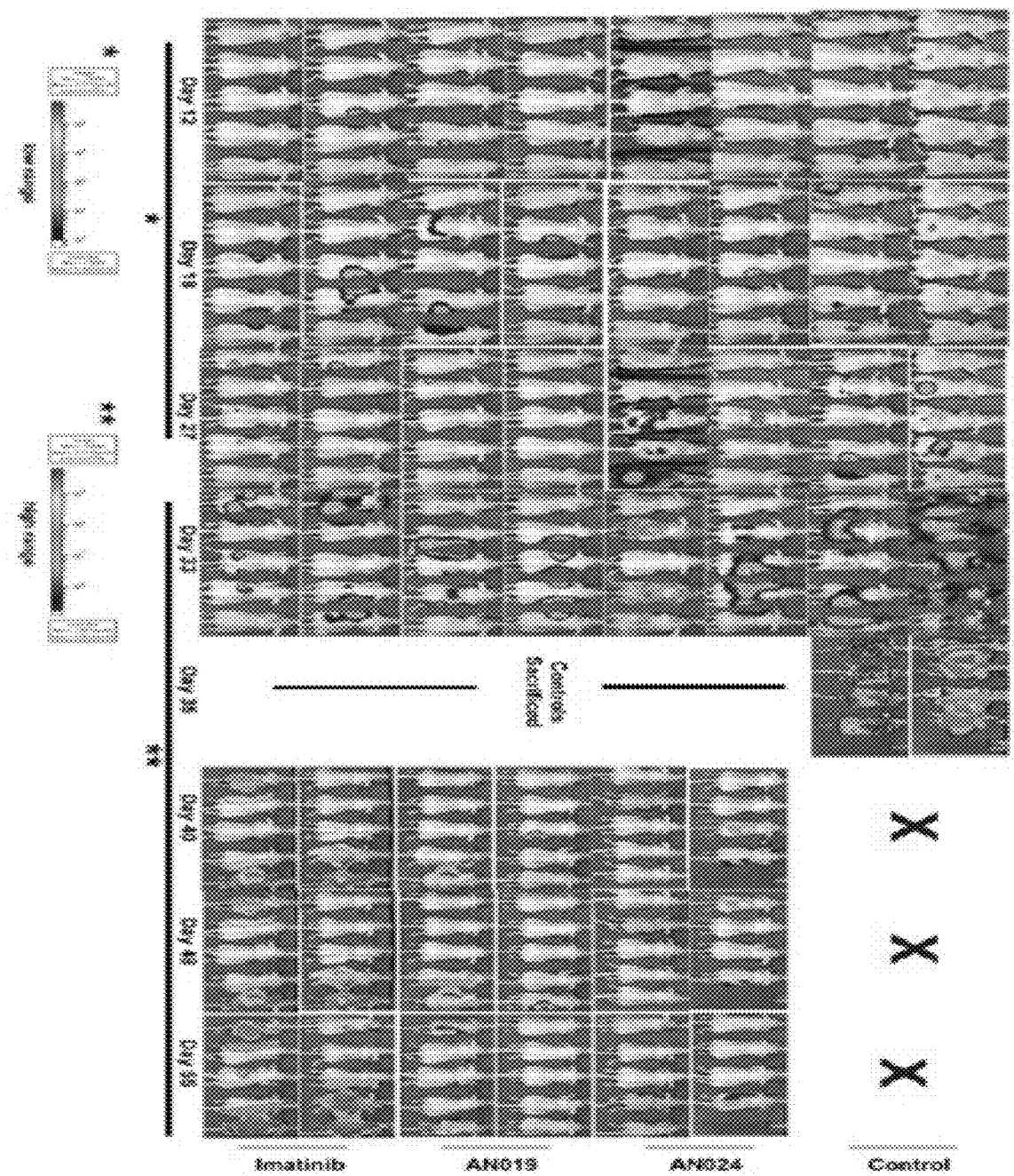
FIG. 6—The percentage inhibition in cell proliferation obtained from the MTT assay is tabulated in the table.
Figure 6B:
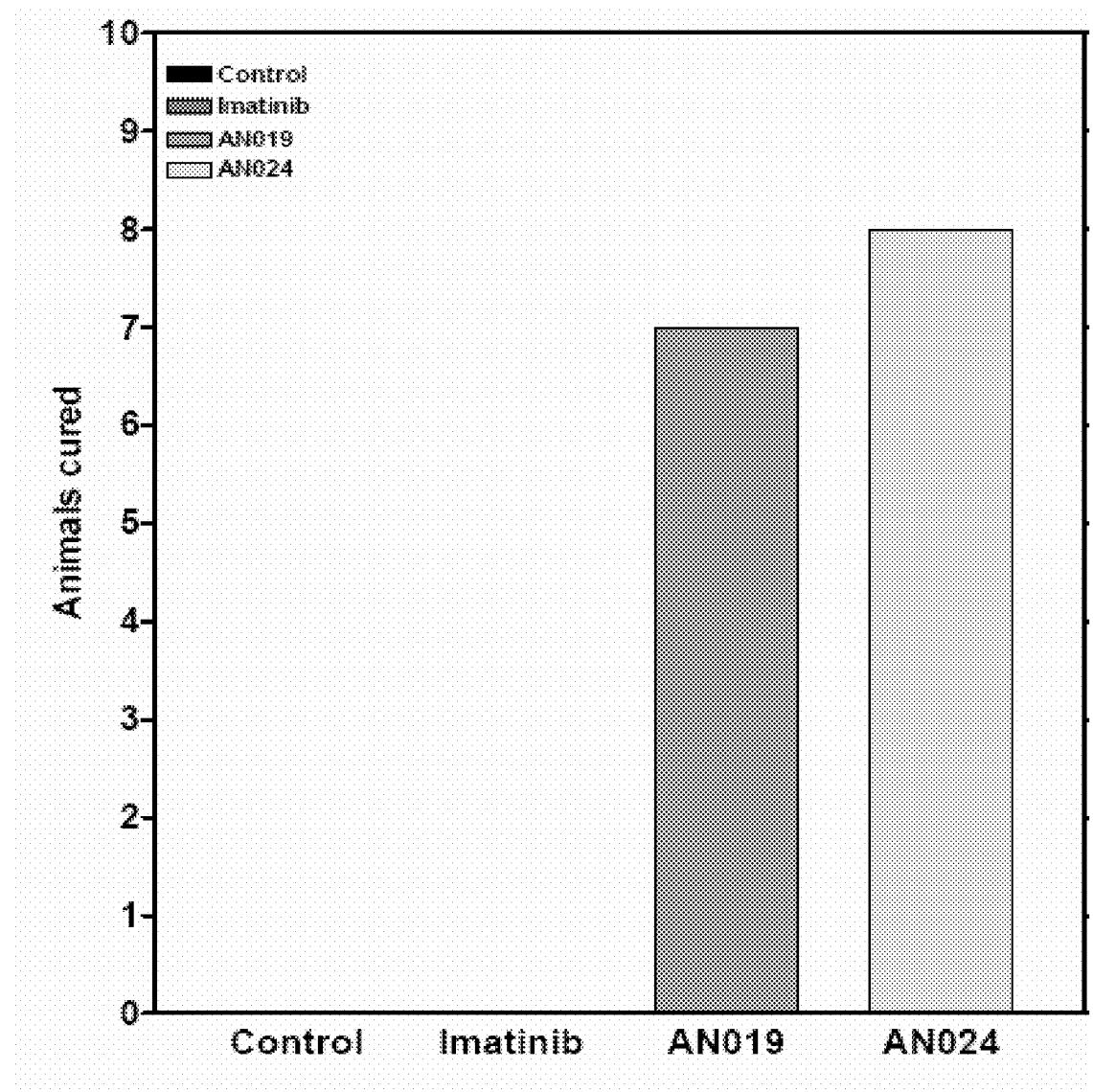
Figure 6C:
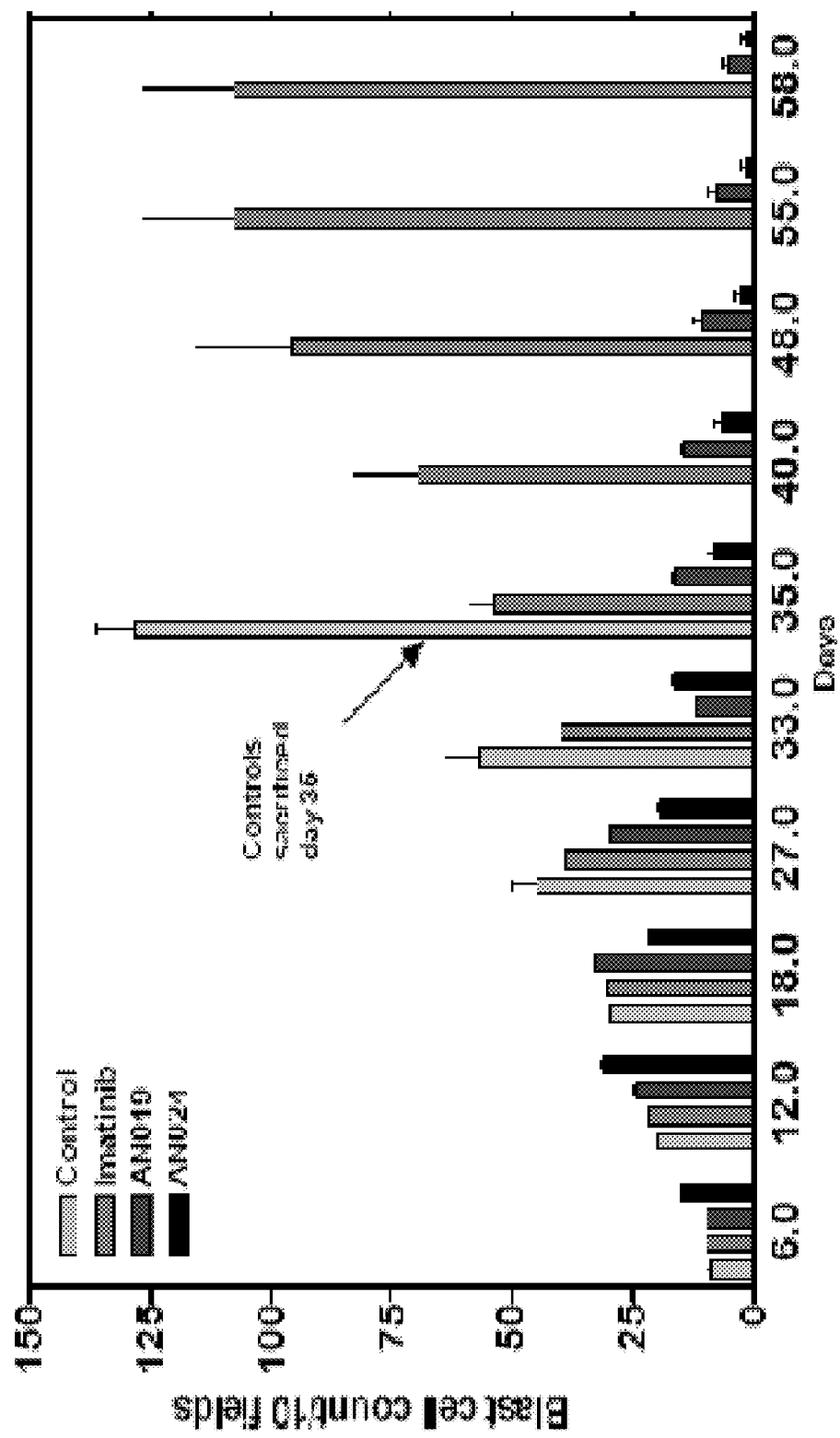
Figure 7A:
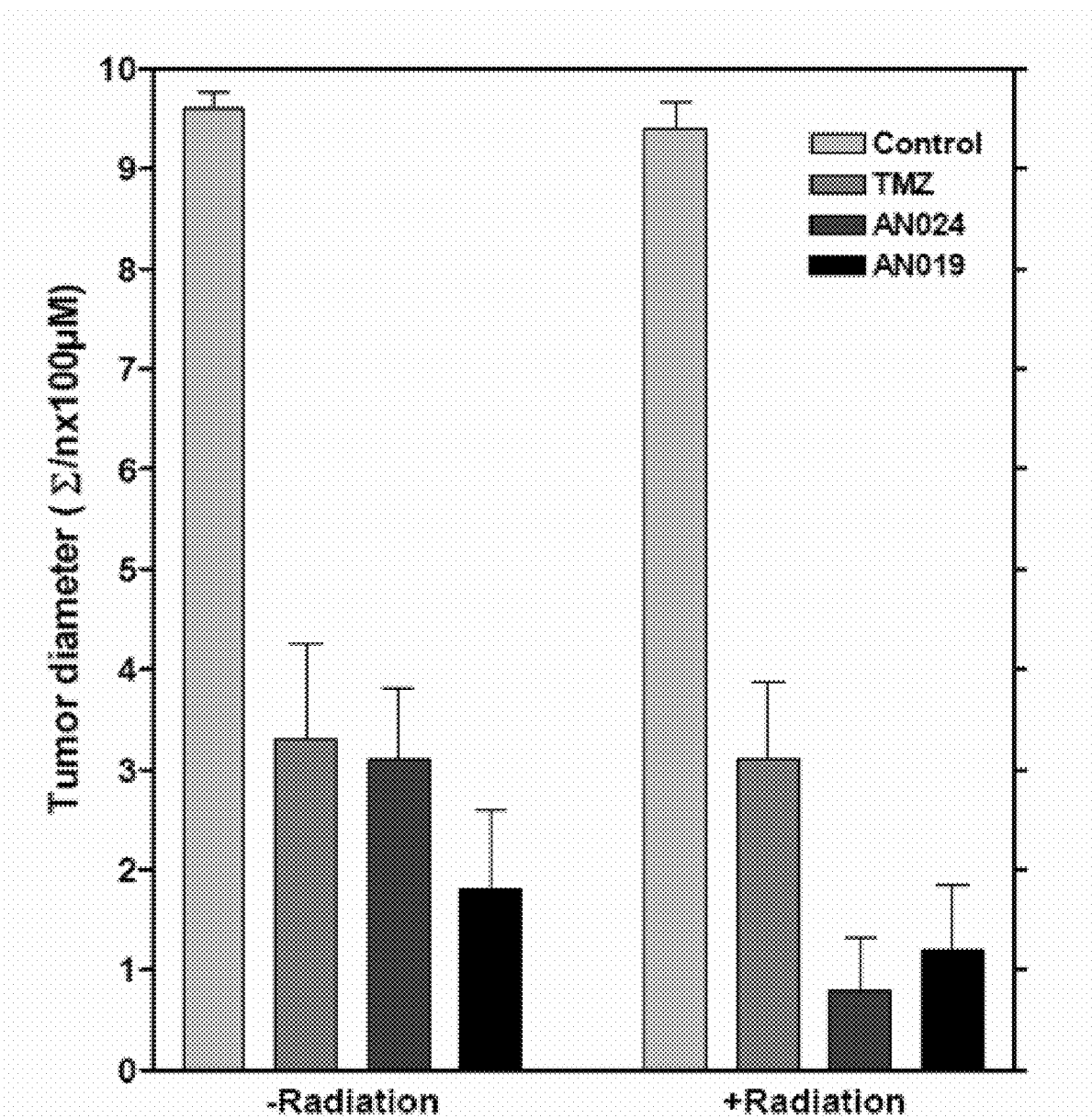
Figure 7B:
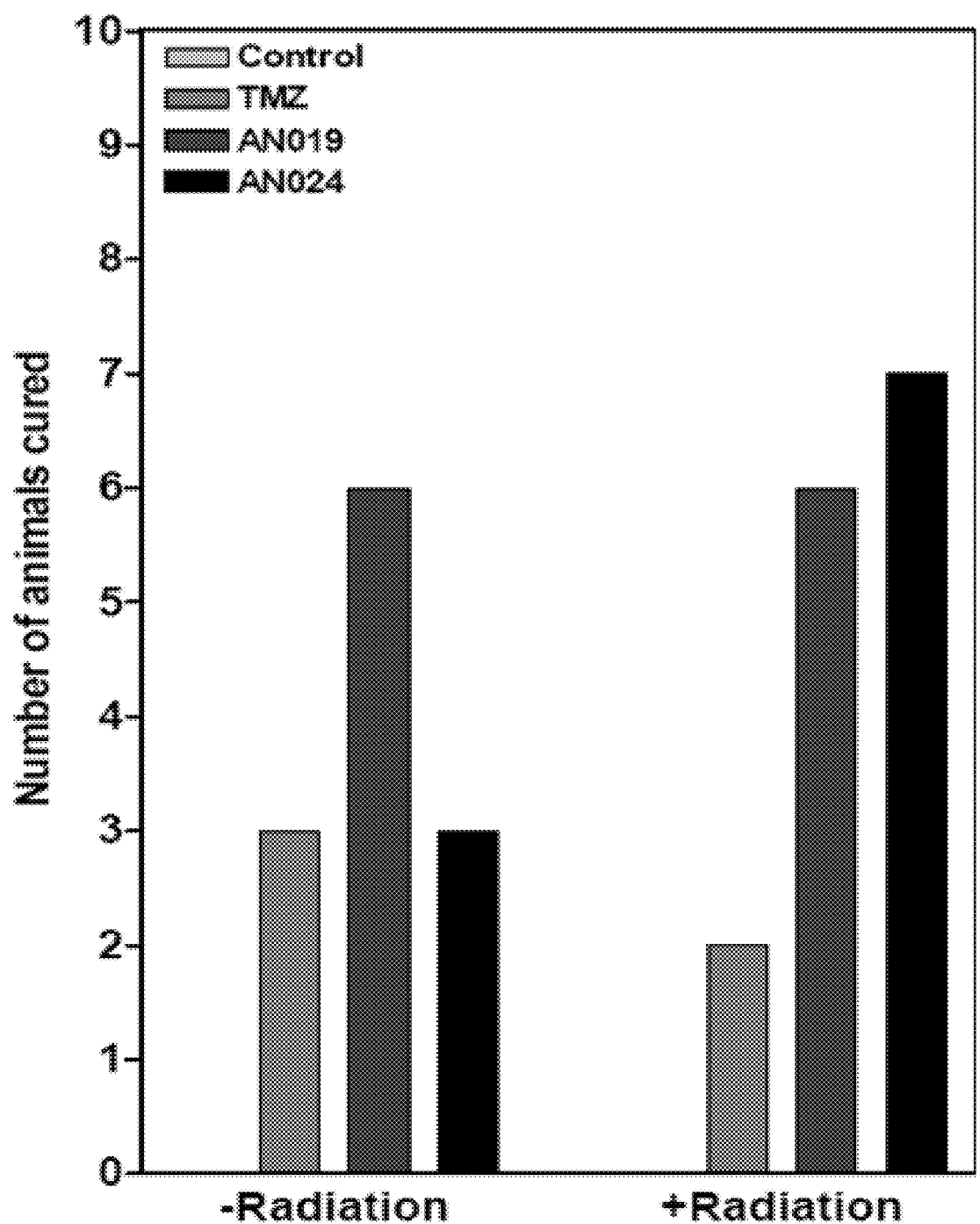

After 48 hrs of the culture, the cells (from CML patients and normal persons) were seeded into 96-well plate at a density of $5 \times 10^3$ cells/well. The compounds of formula (I) prepared by the process described in (Example-1 and Example-3) were added at different concentrations to the cells and were incubated for 24 hrs. After the incubation period, MTT was added to the cells and incubated for additional 3 hrs. The formazan crystals formed were dissolved in lysis buffer and the absorbance was read at a dual wavelength of 570-630 nm. The percent inhibition of cell proliferation was calculated in relation to unreacted cells. The percentage inhibition in cell proliferation obtained from the MTT assay is tabulated in the table (FIG. 6)

Advantages of the Invention:
1. Novel compounds of formula-I and novel intermediates are disclosed
2. Novel compounds of formula-I have been found to be potentially useful therapeutic agents for treatment of CML as evidenced by in vitro and ex-vivo studies.

We claim:
1. A phenyl amino pyrido pyrimidine of formula I

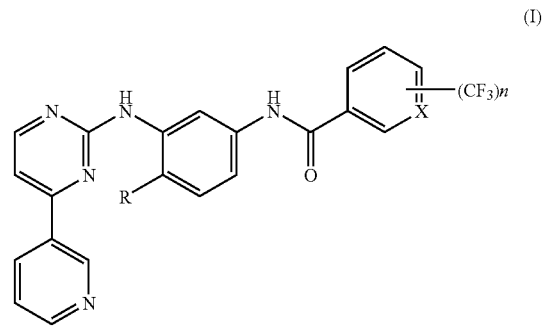

where:
X is CH, n=1 or 2, and R is H or $CH_3$, or
X is N, n=1, and R is H or $CH_3$; or
a pharmaceutically acceptable salt thereof.

2. The compound of claim 1, where X is N, n=1, and R is H $CH_3$; or
a pharmaceutically acceptable salt thereof.

3. The compound of claim 1, where X is CH, n=1 or 2, and R is H or $CH_3$; or
a pharmaceutically acceptable salt thereof.

4. The compound of claim 1, wherein:
when n=1, the trifluoromethyl group is bonded to the aromatic ring at position 3; and
when n=2, the first trifluoromethyl group is bonded to the aromatic ring at position 3 and the second trifluoromethyl group is bonded to the aromatic ring at position 5.

5. The compound of claim 4, where R is $CH_3$.
6. The compound of claim 1:
where R is methyl, X is CH, and n=1; or
where R is methyl, X is CH, and n=2;
where R is methyl, X is N, and n=1.

7. A compound of Formula XV

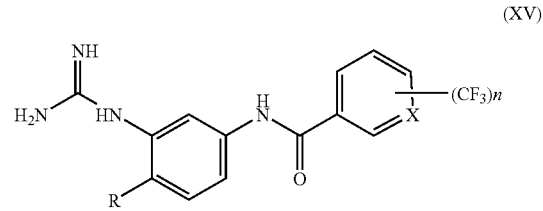

where:
X is CH, n=1 or 2, and R is H or $CH_3$ or
X is N, n=1, and R is H or $CH_3$; or
a pharmaceutically acceptable salt thereof.

8. The compound of claim 7:
where R is methyl, X is CH and n=2;
where R is methyl, X is CH, and n=1;
where R is methyl, X is N and n=1; or
where R is methyl, X is N and n=2.

9. A process of preparing a phenyl amino pyrido pyrimidine of formula I

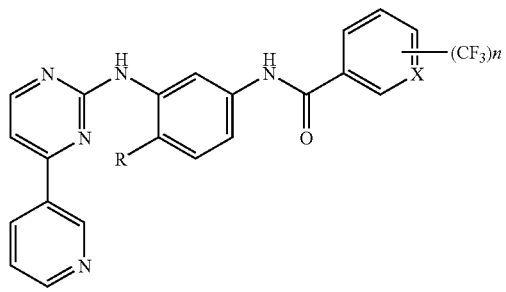
(I)

where:
X is CH, n=1 or 2, and R is H or CH$_3$, or
X is N, n=1, and R is H or CH$_3$; or
a pharmaceutically acceptable salt thereof;
the method comprising:
condensing a 4-methyl-3-nitroaniline of formula XI

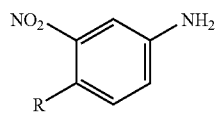
XI where R is as above;
with a trifluoromethyl aroyl chloride of formula XII;

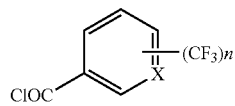
XII where X, n, and Y are as above;
in the presence of a chloro hydrocarbon solvent and a base at a temperature of 30 to 40° C. to yield an intermediate nitro trifluoromethyl aroyl amide of formula XIII

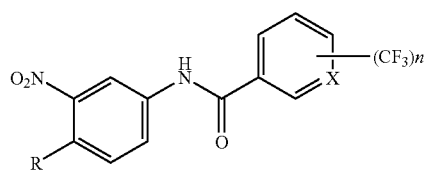
(XIII)

where X, n, R, and Y are as above;
reducing the compound of formula XIII using a metal-acid reducing agent at a temperature of 0-5° C. to yield an intermediate amino trifluoromethyl aroyl amide of formula XIV

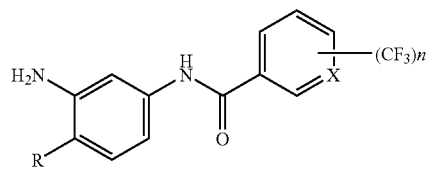
(XIV)

where X n, R, and Y are as above;
condensing the compound of formula XIV with cyanamide (CNNH$_2$) at a temperature of 60 to 95° C. in the presence of polar solvent and an inorganic acid to yield an intermediate salt of a guanidino trifluoromethyl aroyl amide of formula XV

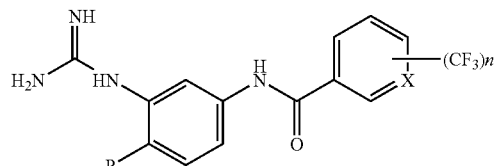
(XV)

where X n, R, and Y are as above; and
condensing the compound of formula XV with a compound of formula XVI

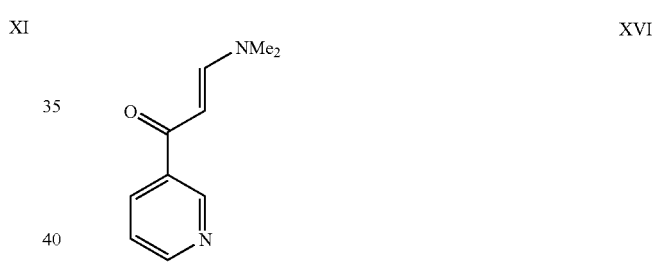
XVI in the presence of a base and at a temperature of 30 to 40° C. to yield the compound of formula I; and
optionally, forming a pharmaceutically acceptable salt the compound of formula I.

10. The process of claim 9, wherein:
the chloro hydrocarbon solvent for condensing the compound of formula XI with the compound of formula XII comprises chloroform, methylene chloride, or ethylene chloride.

11. The process of claim 10, wherein:
the chloro hydrocarbon solvent for condensing the compound of formula XI with the compound of formula XII comprises chloroform.

12. The process of claim 10, wherein the metal-acid reducing agent comprises stannous chloride and concentrated HCl, iron and concentrated HCl, or zinc and concentrated.

13. The process of claim 12, wherein the metal-acid reducing agent comprises stannous chloride and concentrated HCl.

14. The process of claim 9 wherein:
the polar solvent for condensing the compound of formula XIV with cyanamide comprises n-propanol, isopropanol, ethanol, n-butanol, or a mixture thereof.

15. The process of claim 14, wherein the polar solvent for condensing the compound of formula XIV with cyanamide comprises n-butanol.

16. A process of preparing a salt of a guanidino trifluoromethyl aroyl amide of formula XV

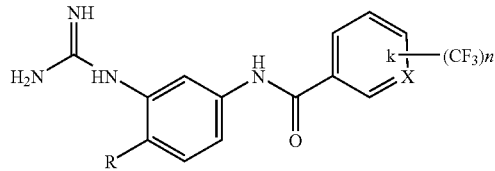

(XV)

where:
X is CH, n=1 or 2, and R is H or CH$_3$, or
X is N, n=1, and R is H or CH$_3$;
the method comprising:
condensing a compound of formula XIV

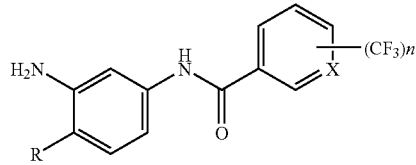

(XIV)

where X n, R, and Y are as above;
with cyanamide (CNNH$_2$) at a temperature of 60 to 95° C. in the presence of polar solvent and an inorganic acid to yield the intermediate salts of a guanidino trifluoromethyl aroyl amide of formula XV.

17. The process of claim 16, wherein:
the polar solvent for condensing the compound of formula XIV with cyanamide comprises n-propanol, isopropanol, ethanol, n-butanol, or a mixture thereof.

18. The process of claim 17, wherein the polar solvent for condensing the compound of formula XIV with cyanamide comprises n-butanol.

19. A process of preparing a phenyl amino pyrido pyrimidine of formula I

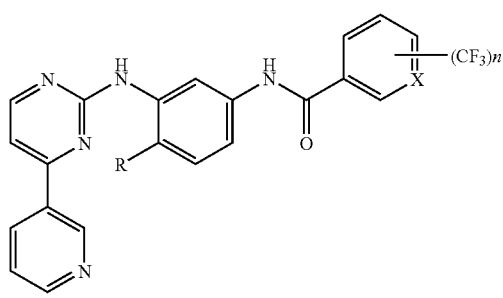

(I)

where:
X is CH, n=1 or 2, and R is H or CH$_3$, or
X is N, n=1, and R is H or CH$_3$; or
a pharmaceutically acceptable salt thereof;
the method comprising:
condensing an N-(5-amino-2-methylphenyl)-4-(3-pyridyl)-2-pyrimidine amine of formula XVII

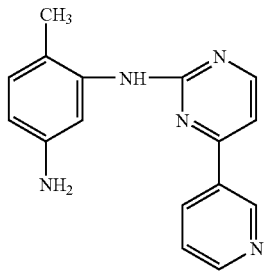

XVII with a trifluoro methyl aroyl chloride of formula XII

XII

ClOC—[benzene ring]—(CF$_3$)$n$ to yield the compound of formula I.

20. A pharmaceutical composition comprising:
a pharmaceutically acceptable carrier; and
a compound for formula 1

(I)

where:
X is CH, n=1 or 2, and R is H or CH$_3$, or
X is N, n=1, and R is H or CH$_3$; or
a pharmaceutically acceptable salt thereof.

21. The pharmaceutical composition of claim 20, wherein:
the pharmaceutically acceptable carrier is suitable for topical, parenteral, or enteral administration.

22. The pharmaceutical composition of claim 20, further comprising an excipient, an adjuvant, a diluent, a binder, a flavoring agent, a flavor enhancer, a pharmaceutically acceptable colorant, or a mixture thereof.

23. The pharmaceutical composition of claim 22, wherein the diluent comprises microcrystalline cellulose, microfine cellulose, lactose, starch, pregelitinized starch, calcium carbonate, calcium sulfate, sugar, dextrate, dextrin, dextrose, dibasic calcium phosphate dihydrate, tribasic calcium phosphate, kaolin, magnesium carbonate, magnesium oxide, maltodextrin, mannitol, polymethacrylate, potassium chloride, powdered cellulose, sodium chloride, sorbitol, talc, or mixture thereof.

24. The pharmaceutical composition of claim 22, wherein the binder comprises acacia, alginic acid, carbomer, carboxymethylcellulose sodium, dextrin, ethyl cellulose, gelatin, guar gum, hydrogenated vegetable oil, hydroxyethyl cellulose, hydroxypropyl cellulose, hydroxypropyl methyl cellulose, liquid glucose, magnesium aluminum silicate, maltodextrin, methylcellulose, polymethacrylate, povidone, pregelatinized starch, sodium alginate, starch, or mixture thereof.

25. The pharmaceutical composition of claim 22, wherein the flavoring agent or the flavor enhancer comprises maltol, vanillin, ethyl vanillin, menthol, citric acid, fumaric acid, ethyl maltol, tartaric acid, or mixture thereof.

26. The pharmaceutical composition of claim 22, comprising compound of formula I, polyvinylpyrrolidone, lactose, talc, crospovidone, magnesium stearate, and sodium laurel sulfate.

27. The compound of claim 1, wherein the compound is:
(3-trifluoromethyl)-N-[4-methyl-3-(4-pyridin-3-yl-pyrimidin-2-ylamino)-phenyl]-benzamide;
(3,5-bis-trifluoromethyl)-N-[4-methyl-3-(4-pyridin-3-yl-pyrimidin-2-ylamino)-phenyl]-benzamide;
(2-trifluoromethyl)-N-[4-methyl-3-(4-pyridin-3-yl-pyrimidin-2-ylamino)-phenyl]-benzamide;
(6-trifluoromethyl)-N-[4-methyl-3-(4-pyridin-3-yl-pyrimidin-2-ylamino)-phenyl]-nicotinamide;
(5-trifluoromethyl)-N-[4-methyl-3-(4-pyridin-3-yl-pyrimidin-2-ylamino)-phenyl]-nicotinamide; or
a pharmaceutically acceptable salt thereof.

28. The compound of claim 1, wherein the compound is (3,5-bis-trifluoromethyl)-N-[4-methyl-3-(4-pyridin-3-yl-pyrimidin-2-ylamino)-phenyl]-benzamide; or a pharmaceutically acceptable salt thereof.

29. The compound of claim 1, wherein the compound is:

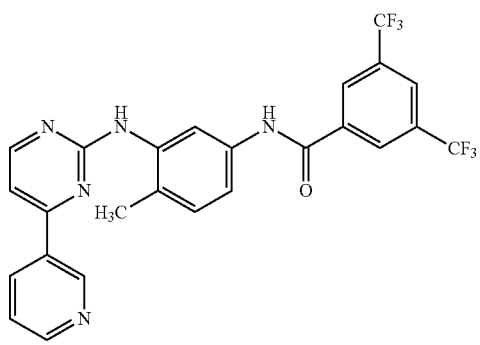

or a pharmaceutically acceptable salt thereof.

30. The compound of claim 7, wherein the compound is:
(3,5-bis-trifluoromethyl)-N-(3-guanidino-4-methyl-phenyl)-benzamide
(3-trifluoromethyl)-N-(3-guanidino-4-methyl-phenyl)-4-benzamide;
(2-trifluoromethyl)-N-(3-guanidino-4-methyl-phenyl)-)-benzamide;
(6-trifluoromethyl)-N-(3-guanidino-4-methyl-phenyl)-nicotinamide;
(5-trifluoromethyl)-N-(3-guanidino-4-methyl-phenyl)-nicotinamide; or
a pharmaceutically acceptable salt thereof.

31. The compound of claim 7, wherein the compound is (3,5-bis-trifluoromethyl)-N-(3-guanidino-4-methyl-phenyl)-benzamide; or a pharmaceutically acceptable salt thereof.

32. The process of claim 9, wherein the base employed in converting the compound of formula XII to the compound of formula XIII comprises triethyl amine, dipropyl amine, or diisopropyl amine.

33. The process of claim 32, wherein the base employed in converting the compound of formula XII to the compound of formula XIII comprises triethyl amine.

34. The process of claim 9 wherein the temperature employed for condensing the compound of formula XIV with cyanamide is 90 to 95° C.

35. The process of claim 16, wherein the temperature employed for condensing the compound of formula XIV with cyanamide is 90 to 95° C.

36. The pharmaceutical composition of claim 20, wherein the pharmaceutically acceptable carrier is inorganic or organic.

37. The pharmaceutical composition of claim 20, wherein the pharmaceutically acceptable carrier is solid or liquid.

38. A compound of formula:

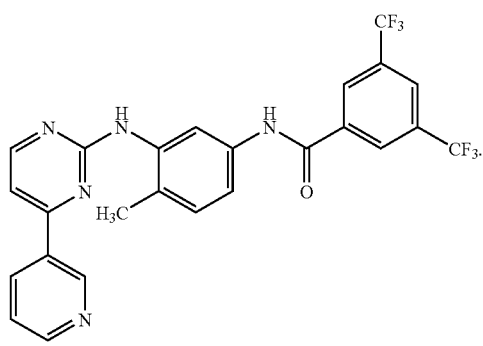

39. A pharmaceutical composition comprising:
a pharmaceutically acceptable carrier; and
a compound of formula:

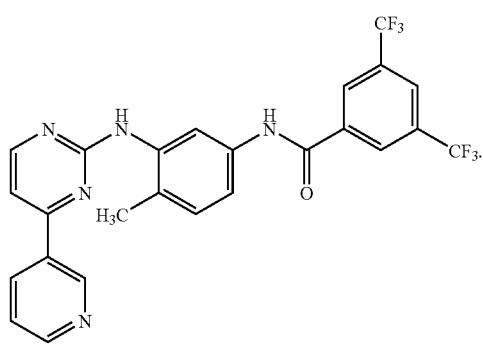

40. The pharmaceutical composition of claim 39, comprising the compound, polyvinylpyrrolidone, lactose, talc, crospovidone, magnesium stearate, and sodium laurel sulfate.

* * * * *